(12) United States Patent
Gilmour et al.

(10) Patent No.: US 11,457,975 B2
(45) Date of Patent: Oct. 4, 2022

(54) APPARATUS AND A METHOD FOR THE TREATMENT OF A PROSTATIC DISEASE

(71) Applicant: Prostacare Pty Ltd., Sydney (AU)

(72) Inventors: Robert Gilmour, Sydney (AU); Thayne Larson, Scottsdale, AZ (US)

(73) Assignee: Prostacare Pty Ltd, Sydney (AU)

( * ) Notice: Subject to any disclaimer, the term of this patent is extended or adjusted under 35 U.S.C. 154(b) by 982 days.

(21) Appl. No.: 16/201,642

(22) Filed: Nov. 27, 2018

(65) Prior Publication Data

US 2019/0159834 A1    May 30, 2019

(30) Foreign Application Priority Data

Nov. 27, 2017  (AU) .................. 2017904778

(51) Int. Cl.
| | |
|---|---|
| *A61B 18/14* | (2006.01) |
| *A61M 25/00* | (2006.01) |
| *A61B 18/00* | (2006.01) |

(52) U.S. Cl.
CPC ..... *A61B 18/1492* (2013.01); *A61M 25/0082* (2013.01); *A61B 2018/0072* (2013.01);
(Continued)

(58) Field of Classification Search
CPC ............ A61B 18/1492; A61B 18/1485; A61B 2018/1475; A61B 2018/1266;
(Continued)

(56) References Cited

U.S. PATENT DOCUMENTS

| | | |
|---|---|---|
| 3,698,394 A | 10/1972 | Piper et al. |
| 3,933,616 A | 1/1976 | Beer |

(Continued)

FOREIGN PATENT DOCUMENTS

| | | |
|---|---|---|
| EP | 1080731 A2 | 3/2001 |
| EP | 2326274 B1 | 8/2009 |

(Continued)

OTHER PUBLICATIONS

A. Plesnicar, G. Sersa, L. Vodovnik, J. Jancar, L. Zaletel-Kragelj and S. Plesnicar. Electric Treatment of Human Melanoma Skin Lesions with Low Level Direct Electric Current: An Assessment of Clinical Experience Following a Preliminary Study in Five Patients, European Journal of Surgery 1994; Suppl 574:45-49.

(Continued)

*Primary Examiner* — Thomas A Giuliani

(74) *Attorney, Agent, or Firm* — Patterson Thuente Pedersen, P.A.

(57) ABSTRACT

Treatments for prostatic disease use a urethral catheter with ports positioned outside a patient. The catheter's lumen has a cross-sectional shape and an electrode assembly with a shaft having a corresponding cross-sectional shape that interlocks with the shape of the lumen. The shaft includes a plurality of shaft channels, an extendable electrode in each channel, and a collar with a protruding flange that interfaces with a port when the electrode assembly is within the lumen. An electrode actuator controls actuation of the electrodes. The collar and actuator are interfaced via a keyed structure. A plurality of ports in the assembly interface with the lumen and project the electrodes outward through the catheter and into the prostate when actuated. The electrodes are extended in a predefined rotational orientation relative to the keyed structure. A power source is coupled to the electrodes and delivers direct current to the prostate.

21 Claims, 18 Drawing Sheets

(52) U.S. Cl.
CPC ............ *A61B 2018/00172* (2013.01); *A61B 2018/00178* (2013.01); *A61B 2018/00214* (2013.01); *A61B 2018/00285* (2013.01); *A61B 2018/00547* (2013.01); *A61B 2018/00577* (2013.01); *A61B 2018/00642* (2013.01); *A61B 2018/00702* (2013.01); *A61B 2018/00791* (2013.01); *A61B 2018/00827* (2013.01); *A61B 2018/143* (2013.01); *A61B 2018/1467* (2013.01); *A61M 2205/054* (2013.01); *A61M 2210/1096* (2013.01)

(58) Field of Classification Search
CPC ........... A61B 2018/00214; A61B 2018/00285; A61B 2018/0022; A61B 2018/00547; A61B 2018/00577; A61B 2018/00642; A61B 2018/143; A61B 2018/1467; A61B 2018/1472; A61B 2018/1425; A61B 2018/1465; A61N 1/30
USPC ........ 606/41, 49; 607/98, 99, 101, 105, 113, 607/115, 116, 143
See application file for complete search history.

(56) References Cited

U.S. PATENT DOCUMENTS

| | | |
|---|---|---|
| 4,003,379 A | 1/1977 | Ellinwood, Jr. |
| 4,026,304 A | 5/1977 | Levy |
| 4,289,135 A | 9/1981 | Nordenstrom et al. |
| 4,572,214 A | 2/1986 | Nordenstrom et al. |
| 4,639,244 A | 1/1987 | Rizk et al. |
| 4,679,561 A | 7/1987 | Doss |
| 4,682,596 A | 7/1987 | Bales et al. |
| 4,721,123 A | 1/1988 | Cosentino et al. |
| 4,919,138 A | 4/1990 | Nordenstrom |
| 4,974,595 A | 12/1990 | Nordenstrom |
| 5,002,558 A | 3/1991 | Klein et al. |
| 5,026,371 A | 6/1991 | Rydell et al. |
| 5,058,605 A | 10/1991 | Slovak |
| 5,084,154 A | 1/1992 | Wakizoe et al. |
| 5,098,843 A | 3/1992 | Calvin |
| 5,281,218 A | 1/1994 | Imran |
| 5,304,214 A | 4/1994 | DeFord et al. |
| 5,314,451 A | 5/1994 | Mulier |
| 5,314,457 A | 5/1994 | Jeutter et al. |
| 5,370,675 A | 12/1994 | Edwards et al. |
| 5,431,625 A | 7/1995 | Fabian et al. |
| 5,458,627 A | 10/1995 | Baranowski |
| 5,482,054 A | 1/1996 | Slater et al. |
| 5,501,662 A | 3/1996 | Hofmann |
| 5,507,724 A | 4/1996 | Hofmann et al. |
| 5,529,574 A | 6/1996 | Frackelton |
| 5,536,240 A | 7/1996 | Edwards et al. |
| 5,536,267 A | 7/1996 | Edwards et al. |
| 5,558,673 A | 9/1996 | Edwards et al. |
| 5,584,872 A | 12/1996 | LaFontaine et al. |
| 5,611,350 A | 3/1997 | John |
| 5,630,426 A | 5/1997 | Eggers et al. |
| 5,672,153 A | 9/1997 | Lax et al. |
| 5,674,267 A | 10/1997 | Mir et al. |
| 5,680,860 A | 10/1997 | Imran |
| 5,701,895 A | 12/1997 | Prutchi et al. |
| 5,718,686 A | 2/1998 | Davis |
| 5,807,306 A | 9/1998 | Shapland et al. |
| 5,810,764 A | 9/1998 | Eggers et al. |
| 5,820,548 A | 10/1998 | Sieben et al. |
| 5,868,741 A | 2/1999 | Chia et al. |
| 5,869,326 A | 2/1999 | Hofmann |
| 5,919,187 A | 7/1999 | Guglielmi et al. |
| 5,931,858 A | 8/1999 | Mackey |
| 5,983,131 A | 11/1999 | Weaver et al. |
| 5,985,305 A | 11/1999 | Peery et al. |
| 5,993,434 A | 11/1999 | Dev et al. |
| 6,009,345 A | 12/1999 | Hofmann |
| 6,016,452 A | 1/2000 | Kasevich |
| 6,021,347 A | 2/2000 | Herbst et al. |
| 6,023,638 A | 2/2000 | Swanson |
| 6,049,733 A | 4/2000 | Phipps et al. |
| 6,051,017 A | 4/2000 | Loeb et al. |
| 6,162,219 A | 12/2000 | Nilsson et al. |
| 6,165,206 A | 12/2000 | Tu |
| 6,169,924 B1 | 1/2001 | Meloy et al. |
| 6,171,787 B1 | 1/2001 | Wiley |
| 6,174,309 B1 | 1/2001 | Wrublewski et al. |
| 6,179,833 B1 | 1/2001 | Taylor |
| 6,238,393 B1 | 5/2001 | Mulier et al. |
| 6,245,068 B1 | 6/2001 | Olson et al. |
| 6,269,270 B1 | 7/2001 | Boveja |
| 6,273,886 B1 | 8/2001 | Edwards |
| 6,278,895 B1 | 8/2001 | Bernard |
| 6,366,808 B1 | 4/2002 | Schroeppel et al. |
| 6,379,353 B1 * | 4/2002 | Nichols .............. A61B 18/1477 606/49 |
| 6,387,075 B1 | 5/2002 | Stivland et al. |
| 6,391,026 B1 | 5/2002 | Hung et al. |
| 6,402,745 B1 | 6/2002 | Wilk |
| 6,419,673 B1 | 7/2002 | Edwards et al. |
| 6,464,699 B1 | 10/2002 | Swanson |
| 6,591,133 B1 | 7/2003 | Joshi |
| 6,595,989 B1 | 7/2003 | Schaer |
| 6,599,274 B1 | 7/2003 | Kucharczyk et al. |
| 6,600,953 B2 | 7/2003 | Flesler et al. |
| 6,607,528 B1 | 8/2003 | Quick et al. |
| 6,626,899 B2 | 9/2003 | Houser et al. |
| 6,638,273 B1 | 10/2003 | Farley et al. |
| 6,638,275 B1 | 10/2003 | McGaffigan et al. |
| 6,708,066 B2 | 3/2004 | Herbst et al. |
| 6,713,291 B2 | 3/2004 | King et al. |
| 6,733,485 B1 | 5/2004 | Whitehurst et al. |
| 6,738,663 B2 | 5/2004 | Schroeppel et al. |
| 6,901,296 B1 | 5/2005 | Whitehurst et al. |
| 6,952,615 B2 | 10/2005 | Satake |
| 7,079,890 B2 | 7/2006 | Ahn et al. |
| 7,412,285 B2 | 8/2008 | Schroeppel et al. |
| 7,556,624 B2 | 7/2009 | Laufer et al. |
| 7,720,549 B2 | 5/2010 | Schroeppel et al. |
| 7,742,811 B2 | 6/2010 | Schroeppel et al. |
| 7,837,670 B2 | 11/2010 | Barath |
| 8,014,854 B2 | 9/2011 | Schroeppel et al. |
| 8,024,048 B2 | 9/2011 | Schroeppel et al. |
| 8,880,195 B2 * | 11/2014 | Azure ................ A61B 18/1477 607/148 |
| 9,211,155 B2 | 12/2015 | Fruland et al. |
| 9,597,145 B2 | 3/2017 | Nelson et al. |
| 10,004,551 B2 | 6/2018 | Burnett |
| 10,085,800 B2 | 10/2018 | Nelson et al. |
| 10,575,899 B2 | 3/2020 | Fruland et al. |
| 10,736,689 B2 | 8/2020 | Sundquist et al. |
| 10,842,555 B2 | 11/2020 | Holtz et al. |
| 10,939,957 B2 | 3/2021 | Nelson et al. |
| 2001/0001314 A1 | 5/2001 | Davison et al. |
| 2001/0021868 A1 | 9/2001 | Herbst et al. |
| 2001/0034518 A1 | 10/2001 | Edwards et al. |
| 2002/0002329 A1 | 1/2002 | Avitall |
| 2002/0026188 A1 | 2/2002 | Balbierz et al. |
| 2002/0077676 A1 | 6/2002 | Schroeppel et al. |
| 2002/0111618 A1 | 8/2002 | Stewart et al. |
| 2002/0115957 A1 | 8/2002 | Sun et al. |
| 2002/0183735 A1 | 12/2002 | Edwards et al. |
| 2003/0130711 A1 | 7/2003 | Pearson et al. |
| 2003/0191504 A1 | 10/2003 | Meadows et al. |
| 2003/0212394 A1 | 11/2003 | Pearson et al. |
| 2004/0010290 A1 | 1/2004 | Schroeppel et al. |
| 2004/0030334 A1 | 2/2004 | Quick et al. |
| 2004/0059326 A1 | 3/2004 | Flores |
| 2004/0172089 A1 | 9/2004 | Whitehurst et al. |
| 2004/0254618 A1 | 12/2004 | Schroeppel et al. |
| 2005/0004438 A1 | 1/2005 | Ward et al. |
| 2005/0004507 A1 | 1/2005 | Schroeppel et al. |
| 2005/0010203 A1 | 1/2005 | Edwards et al. |
| 2005/0054994 A1 | 3/2005 | Cioanta et al. |
| 2005/0080409 A1 | 4/2005 | Young et al. |
| 2005/0131508 A1 | 6/2005 | Garabedian et al. |

(56) References Cited

U.S. PATENT DOCUMENTS

| | | |
|---|---|---|
| 2005/0159742 A1 | 7/2005 | Lesh |
| 2005/0182449 A1 | 8/2005 | Auge et al. |
| 2005/0197657 A1 | 9/2005 | Goth et al. |
| 2005/0222623 A1 | 10/2005 | Kroll et al. |
| 2005/0222646 A1 | 10/2005 | Kroll et al. |
| 2005/0228373 A1 | 10/2005 | Kelly et al. |
| 2005/0245923 A1 | 11/2005 | Christopherson et al. |
| 2005/0283125 A1 | 12/2005 | Barkhahn et al. |
| 2005/0288730 A1 | 12/2005 | Deem et al. |
| 2006/0025756 A1 | 2/2006 | Francischelli et al. |
| 2006/0095032 A1 | 5/2006 | Jackson et al. |
| 2006/0235286 A1 | 10/2006 | Stone et al. |
| 2006/0259027 A1 | 11/2006 | Kwan et al. |
| 2007/0016067 A1 | 1/2007 | Webster, III et al. |
| 2007/0073391 A1 | 3/2007 | Bourang et al. |
| 2007/0179491 A1 | 8/2007 | Kratoksa et al. |
| 2007/0191925 A1 | 8/2007 | Dorn |
| 2007/0255207 A1 | 11/2007 | Hangai et al. |
| 2007/0260234 A1 | 11/2007 | McCullagh et al. |
| 2008/0021275 A1 | 1/2008 | Tearney et al. |
| 2008/0021445 A1 | 1/2008 | Elmouelhi et al. |
| 2008/0027379 A1 | 1/2008 | Wilkins |
| 2008/0071262 A1 | 3/2008 | Azure |
| 2008/0132885 A1 | 6/2008 | Rubinsky et al. |
| 2008/0161804 A1 | 7/2008 | Rioux et al. |
| 2008/0243116 A1 | 10/2008 | Anderson |
| 2009/0024075 A1 | 1/2009 | Schroeppel et al. |
| 2010/0049031 A1 | 2/2010 | Fruland et al. |
| 2010/0049188 A1 | 2/2010 | Nelson et al. |
| 2010/0049192 A1* | 2/2010 | Holtz ............... A61B 18/1815 606/41 |
| 2010/0145325 A1 | 6/2010 | Hoey et al. |
| 2010/0168777 A1 | 7/2010 | Stangenes et al. |
| 2011/0106072 A1 | 5/2011 | Sundquist et al. |
| 2011/0166569 A1 | 7/2011 | Whayne et al. |
| 2011/0208022 A1 | 8/2011 | Brawer et al. |
| 2011/0224663 A1 | 9/2011 | Heim et al. |
| 2012/0203307 A1 | 8/2012 | Schroeppel et al. |
| 2014/0005676 A1 | 1/2014 | Shelton, IV et al. |
| 2016/0184039 A1 | 6/2016 | Shelton, IV et al. |
| 2016/0206370 A1 | 7/2016 | Fruland et al. |
| 2017/0231693 A1 | 8/2017 | Nelson et al. |
| 2019/0021779 A1 | 1/2019 | Govari |
| 2019/0105103 A1 | 4/2019 | Fruland et al. |
| 2020/0022748 A1 | 1/2020 | Kroll et al. |

FOREIGN PATENT DOCUMENTS

| | | |
|---|---|---|
| WO | WO 1997/036632 A1 | 10/1997 |
| WO | WO 1998/047562 A1 | 10/1998 |
| WO | WO 2001/049195 A1 | 7/2001 |
| WO | WO 2001/052931 A1 | 7/2001 |
| WO | WO 2001/062336 A1 | 8/2001 |
| WO | WO 2002/098501 A2 | 12/2002 |
| WO | WO 2005/086683 A2 | 9/2005 |
| WO | WO 2006/042117 A2 | 4/2006 |
| WO | WO 2008/083407 A1 | 7/2008 |
| WO | WO 2010/022275 A1 | 2/2010 |
| WO | WO 2010/022278 A1 | 2/2010 |
| WO | WO 2010/081730 A1 | 7/2010 |

OTHER PUBLICATIONS

A.L. Vandenbogaerde, E.M. Delaey, A.M. Vantieghem, B.E. Himpens, W.J. Merlevede, P.A. de Witte, Abstract of Cytotoxicity and Antiproliferative Effect of Hypericin and Derivatives After Photosensitization. Photochem Photobiol Jan. 1998;67(1):119-25.

B. Wolf, M. Brischwein, W. Baumann, R. Ehret, T. Henning, M. Lehmann, A. Schwinde. Microsensor-Aided Measurements of Cellular Signalling and Metabolism on Tumor Cells, Tumor Biology 1998; 19:374-383.

B.N. Singh and C. Dwivedi. Antitumor Drug Delivery by Tissue Electroporation, Anti-Cancer Drugs 1999, 10, pp. 139-146.

Belehradek, J.J., Orlowski, S., Raimiriz, L.H., Pron, G., Poddevin, B. and Mir, L.M., "Electropermeabilization of cells and tissues assessed by the qualitative and quantitative electroloading of bleomycin", Biochem. Biophys. Acta, vol. 1190, pp. 155-163, 1994.

Berendson J. Simonsson D. Electrochemical aspects of treatment of tissue with direct current. Eur J Surg 1994: Suppl 574: 111-115.

Buchwald H, Rohde TD. Implantable pumps. Recent progress and anticipated future advances. ASAIO J 1992; 38 No. 4: 772-778.

C. Hauton, M. Charbonnier, L. Cara and J.P. Salles, A New Type of Liposome for Electrochemical Treatment of Cancer: The Lipogelosomes, European Journal of Surgery 1994; Suppl 574: 117-119.

C.E. Humphrey, E.H. Seal. Biophysical Approach toward Tumor Regression in Mice, Science, vol. 130, 1959.

Chen B, Xie Z, Zhu F. Experimental study on electrochemical treatment of cancer in mice. Eur J Surg 1994; Suppl 574: 75-77.

Chou C, McDougall JA, Ahn C, Vora N. Electrochemical treatment of mouse and rat fibrosarcomas with direct current. Bioelectromagnetics 1997; 18: 14-24.

D. Liu, Y.L. Xin, B. Ge, F. Zhao, H.C. Zhso. Experimental Studies on Electrolytic Dosage of ECT for Dog's Oesophageal Injury and Clinical Effects of ECT for Oesopohageal Anastomotic Opening Stenosis and Oesophageal Carcinoma, European Journal of Surgery 1994; Suppl 574: 71-72.

D. Miklavcic, D. An, J. Belehradek, Jr., L.M. Mir. Abstract of Host's Immune Response in Electrotherapy of Murine Tumors by Direct Current, European Cytokine Network Sep. 1997;8(3):275-9.

D.M. Morris, M.D., A.A. Marino, Ph. D., and E. Gonzalez, M.D. Electrochemical Modification of Tumor Growth in Mice, Journal of Surgical Research 53, 306-309 (1992).

Damascelli B, Patelli G, Frigerio LF, Lanocita R, Di Tolla GD, Marchiano A., Spreafico C, Garbagnati F, Bonalumi MG, Monfardini L Ticha V, Prino A. First clinical experience with a high-capacity implantable infusion pump for continuous intravenous chemotherapy. Cardiovasc Intervent Radiol 1999; 22:37-43.

E. Nilsson. Modelling of the Electrochemical Treatment of Tumours. Dissertation, Department of Chemical Engineering and Technology, Applied Electrochemistry, Royal Institute of Technology, Stockholm 2000.

Electro-Cancer Treatment, http://www.st-georg.com/ect.html, retrieved Oct. 25, 1999.

G. Sersa, M. Cemazar, D. Miklavcic and D. J. Chaplin, Tumor Blood Flow Modifying Effect of Electrochemotherapy with Bleomycin, Anticancer Research 19: 4017-4022 (1999).

G.D. O'Clock, Ph. D. (E.E.), P.E. The Effects of In Vitro Electrical Stimulation on Eukaryotic Cells: Suppression of Malignant Cell Proliferation, Journal of Orthomolecular Medicine, vol. 12, No. 3, 1997.

H. Gong, G. Liu. Effect of Electrochemical Therapy on Immune Functions of Normal and Tumour-Bearing Mice, European Journal of Surgery, Suppl 1994; (574): 73-74.

H. von Euler, Electrochemical Treatment of Tumours, Doctoral Thesis, Swedish University of Agricultural Sciences, Uppsala 2002.

Habal and Schauble. An implantable DC power unit for control of experimental tumor growth in hamsters. Medical Instrumentation 7 No. 5: 305-306. (1973).

Heruth KT, Medtronic SynchroMed drug administration system. Ann NY Acad Sci 1988; 531: 72-75.

Hofmann, Dev, Nanda, and Rabussay. electroporation therapy of solid tumors. Critical Reviews in therapeutic Drug Carrier Systems 16(6):523-569 (1999).

Hofmann, G.A., Dev. S.B., Dimmer, S. and Nanda, G.S., "Electroporation Therapy: A new approach to the treatment of head and neck cancer, IEEE Transactions on Biomedical Engineering", vol. 46, No. 6, pp. 752-759, 1999.

http://www.genetronics, retrieved Jul. 29, 2003.

J.C. Weaver. Electroporation: A General Phenomenom for Manipulating Cells and Tissues. J Cell Biochem 1993; 51 No. 4: 426-435.

K. Brandisky, I. Daskalov. Abstract of Electrical Field and Current Distributions in Electrochemotherapy, Bioelectrochemistry and Bioenergetics Feb. 1999; 48(1):201-8.

Kirsch DL, Lerner FN. Electromedicine: the other side of physiology. In: Innovations in pain management: a practical guide for clinicians. Winter Park, FL: GR Press, 1995.

(56) References Cited

OTHER PUBLICATIONS

L. Vodovnik, D. Miklavcic, G. Sersa. Modified Cell Proliferation Due to Electrical Currents, Medical and Biological Engineering and Computing, 1992, 30, CE21-CE28.

L.F. Glass, N.A. Fenske, M. Jaroszeski, R. Perrott, D.T. Harvey, D.S. Reintgen, R. Heller. Abstract of Bleomycin-Mediated Electrochemotherapy of Basal Cell Carcinoma, Journal of the American Academy of Dermatology Jan. 1996; 34(1):82-6.

L.H. Ramirez, S. Orlowski, D. An, G. Bindoula, R. Dzodic, P. Ardouin, C. Bognel, J. Belehradek Jr., J-N Munck, and L.M. Mir. Electrochemotherapy on Liver Tumours in Rabbits, British Journal of Cancer (1998) 77(12). 2104-2111.

Lao, Y., Ge, T., Zheng, X., Zhang, J. Hua, Y., Mao, S., Feng, X. Electrochemical therapy for intermediate and advanced liver cancer: a report of 50 cases. Eur J Surg 1994; Suppl 574: 51-53.

Li K, Xin Y, Gu Y, Xu B, Fan D. Ni B. Effects of direct current on dog liver: possible mechanisms for tumor electrochemical treatment. Bioelectromagnetics 1997; 18: 2-7.

M. Belehradek, C. Domenge, B. Luboinski, S. Orlowski, J. Belehradek, Jr., L.M. MIR. Abstract of Electrochemotherapy, A new antitumor treatment. First clinical phase I-II trial. Cancer Dec. 15, 1993; 72(12):3694-700.

M. Cemazar, G. Sersa and D. Miklavcic. Electrochemotherapy with Cisplatin in the Treatment of Tumor Cells Resistant to Cisplatin, Anticancer Research 18:4463-4466 (1998).

M. Kraus and B. Wolf. Implications of Acidic Tumor Microenvironment for Neoplastic Growth and Cancer Treatment: A Computer Analysis, Tumor Biology 1996; 17: 133-154.

M. Kraus and B. Wolf. Physicochemical Microenvironment as Key Regulator for Tumor Microevolution, Invasion, and Immune Response: Targets for Endocytotechnological Approaches in Cancer Treatment, Endocytobiosis & Cell Research, 12, 133-156 (1998).

M. Wojcicki, R. Kostyrka, B. Kaczmarek, J. Kordowski, M. Romanowski, M. Kaminski, J. Klonek, S. Zielinski. Abstract of Electrochemical Therapy in Palliative Treatment of Malignant Dysphagia: A Pilot Study, Hepatogastroenterology Jan.-Feb. 1999;46(25):278-84.

M.A. Hamza, P.F. White, H.E. Ahmed, E.A. Ghoname. Abstract of Effect of the Frequency of Transcutaneous Electrical Nerve Stimulation on the Postoperative Opioid Analgesic Requirement and Recovery Profile, Anesthesiology Nov. 1999;91(5):1232-8.

M.B. Habal. Abstract of Effect of Applied DC Currents on Experimental Tumor Growth in Rats, Journal of Biomedical Materials Research, vol. 14, 789-801 (1980).

M.K. Schauble, M.B. Habal. Electropotentials of Tumor Tissues. Journal of Surgical Research 9: 9, 1969.

Matsushima Y, Takahashi E, Hagiwara K, Konaka C, Miura H, Kato H, Koshiishi Y. Clinical and experimental studies of anti-tumoural effects of electrochemical therapy (ECT) alone or in combination with chemotherapy. Eur J Surg 1994; Suppl 574: 59-67.

Mir LM, Orlowski S, Belehradek Jr J, Paoletti C. Electrochemotherapy potentiation of antitumour effect of bleomycin by local electric pulses. Eur J Cancer 1991; 27:68-72.

N. Raghunand. Abstract of pH and Chemotherapy, Symposium 240: The Tumour Microenvironment: Causes and Consequences of Hypoxia and Acidity, p. 5-6, held at the Novartis Foundation, London, 240 Oct. 10-12, 2000.

Nordenstrom B. Biologically closed electric circuits: activation of vascular interstitial closed electric circuits for treatment of inoperable cancer. Journal of Bioelectricity 1984; 3(162): 137-153.

Nordenstrom B. Preliminary clinical trials of electrophoretic ionization in the treatment of malignant tumors. IRCS Med Sc 1978; 6: 537.

Nordenstrom BEW, Eksborg, S., Beving, H. Electrochemical treatment of cancer. II: effect of electrophoretic influence on adriamycin. Am J Clin Oncol (CCT)1990; 13(1): 75-88.

Nordenstrom BEW. Biologically closed electric circuits: clinical, experimental and theoretical evidence for an additional circulatory system. Stockholm: Nordic Medical Publications, 1983.

Nordenstrom BEW. Electrochemical treatment of cancer. I: variable response to anodic and cathodic fields. Am J Clin Oncol (CCT) 1989; 12(6): 530-536.

Nordenstrom BEW. Survey of mechanisms in electrochemical treatment (ECT) of cancer. Eur J Surg 1994: Suppl 574: 93-109.

Okino, M. and Mohri, H. Effects of a high voltage electrical impulse and an anti-cancer drug on In Vivo growing tumors. Japanese Journal of Cancer Research, vol. 78, pp. 1319-1321, 1987.

Orlowski, S., Belehradek, J. J., Paoletti,C. and Mir, L.M. "Transient electropermeabilization of cells in culture increase of the cytotoxicity of anti-cancer drugs", Biochem, vol. 37, No. 24, pp. 4727-4733, 1988.

P. Vaupel, D.K. Kelleher, M. Hockel. Abstract of Oxygen Status of Malignant tumors: Pathogenesis of Hypoxia and Significance for Tumor Therapy. Semin Oncol Apr. 2001; 28(2 Suppl 8):29-35.

Quan, K. Analysis of the clinical effectiveness of 144 cases of soft tissue and superficial malignant tumors treated with electrochemical therapy. Eur J Surg 1994; Suppl 574: 37-40.

R.A. Gatenby. Abstract of Mathematical Models of Tumour Invasion Mediated by Transformation-Induced Alteration of Microenvironment pH, Symposium 240: The Tumour Microenvironment: Causes and Consequences of Hypoxia and Acidity, p. 2-3, held at the Novartis Foundation, London, 240 Oct. 10-12, 2000.

Ranade VV. Drug delivery systems. 4. Implants in drug delivery. J Clin Pharmacol 1990; 30 No. 10: 871-889.

Reis A, Henninger T. Zerstorung maligner Wachstumsenergie durch anodische Oxydation. Kim Wochenschrift 1951; _: 39.

S. Seguchi, S. Kawauchi, Y. Morimoto, T. Arai, H. Asanuma, M. Hayakawa, M. Kikuchi. Abstract of Critical Parameters in the Cytotoxicity of Photodynamic Therapy Using a Pulsed Laser. Lasers Med Sci 2002, 17(4):265-71.

S.A. Grossman, P.S. Staats, Abstract of Current Management of Pain in Patients with Cancer. Oncology (Huntingt) Mar. 1994; 8(3):93-107.

S.L. David, D.R. Absolom, C.R. Smith, J. Gams, and M.A. Herbert. Effect of Low Level Direct Current on In Vivo Tumor Growth in Hamsters, Cancer Research 45, 5625-5631, Nov. 1985.

Samuelsson, Harnek, Ewers, Jonsson. Electrochemical and megavolt treatment of rat tumors. Eur J Surg Suppl 574:69-70. (1994).

Schauble MK, Mutaz HB, Gallick HD. Inhibition of experimental tumor growth in hamsters by small direct currents. Arch Pathol Lab Med 1977; 101: 294.

Schecter, DC. "Containment of Tumors Through Electricity." PACE 1979. vol. 2, pp. 100-114.

Semrov and Miklacic. Calculation of the electrical parameters in electrochemistry of solid tumors in mice. Comp Biol Med 28:439-448. (2000).

Sersa, et al. Improvement of Combined modality therapy with cisplatin and radiation using electroporation of tumors. Int J. Radiation Oncology Biol. Phys. vol. 46, No. 4:1037-1041. (2000).

Song Y, Li C, Li Y, Song Q. Chang B, Song L. Liu C. Wang T. Electrochemical therapy in the treatment of malignant tumors on the body surface. Eur J Surg 1994; Suppl 574: 41-43.

Song, L., Liu, C., Zhang, B., Wang, T., Song, Y., Li, Y. Electrochemical therapy (ECT) for thyroid adenoma during acupuncture anaesthesia: analysis of 46 patients. Eur J Surg 1994; Suppl 574: 79-81.

Srinivasan S, Gahen Jr. GL, Stoner GE. Electrochemistry in the biomedical sciences. In: Bloom H, Gutmann F (eds): Electrochemistry the last thirty and the next thirty years. New York: Plenum Press, 1977.

T. Nishi, S.B. Dev., K. Yoshizato, J. Kuratsu, Y. Ushio. Abstract of Treatment of Cancer Using Pulsed Electric Field in Combination With Chemotherapeutic Agents or Genes, Human Cell Mar. 1997;10(1):81-6.

T.V. Taylor, P. Engler, B.R. Pullan and S. Holt. Ablation of Neoplasia by Direct Current, British Journal of Cancer (1994), 70, 342-345.

Turler, Schaefer, et al. Local treatment of hepatic metastases with low level direct electric current: experimental results. Scand J Gastroenterol. 3:322-328. (2000).

(56) References Cited

OTHER PUBLICATIONS

Vogelzang NJ, Ruane M, DeMeester TR. Phase I trial of an implanted battery-powered, programmable drug delivery system for continuous doxorubicin administration. J Clin Oncol 1985; 3 No. 3: 407-414.

W.R. Panje, M.P. Hier, G.R. Garman, E. Harrell, A. Goldman, I. Bloch. Abstract of Electroporation Therapy of Head and Neck Cancer, Annals of Otology, Rhinology and Laryngology Sep. 1998; 107(9 Pt 1): 779-85.

Wang, H. Electrochemical therapy of 74 cases of liver cancer. Eur J Surg 1994; Suppl 574: 55-57.

Wigness BD, Dorman FD, Robinson Jr HJ, Arendt EA, Oegema Jr TR, Rohde TD, Buchwald H. Catheter with an anchoring tip for chronic joint capsule perfusion, ASAIO Trans. 1991; 37 No. 3: M290-292.

Wolf B, Kraus M, and Sieben U, "Potential of microsensor-based feedback bioactuators for biophysical cancer treatment," Biosensors and Bioelectronics, vol. 12, No. 4, pp. 301-309, 1997.

X.Z. Lin, C.M. Jen, C.K. Choud, D.S. Chou, M.J. Sung, T.C. Chou. Saturated Saline Enhances the Effect of Electrochemical Therapy. Digestive Diseases and Sciences 2000: 45(3): 509-514.

Xin Y, Xue F, Ge B, Zhao F, Shi B, Zhang W. Electrochemical treatment of lung cancer. Bioelectromagnetics 1997; 18: 8-13.

Xin, Y. Organisation and spread of electrochemical therapy (ECT) in China. Eur J Surg 1994; Suppl 577: 25-30.

Y. Yen, J.R. Li, B.S. Zhou, F. Rojas, J. Yu and C.K. Chou. Electrochemical Treatment of Human KB Cells In Vitro, Bioelectromagnetics 20:34-41 (1999).

Y.L. Xin, D. Liu. Electrostatic Therapy (EST) of Lung Cancer and Pulmonary Metastasis: Report of 15 Cases. European Journal of Surgery 1994; Suppl 574: 91-92.

Y.L. Xin, F.Z. Xue, F.G. Zhao. Effectiveness of Electrochemical Therapy in the Treatment of Lung Cancers of Middle and Late Stage, Chinese Medical Journal 1997 110(5): 379-383.

Yokoyama, M., Itaoka, T., Nakajima, H., Ikeda, T., Ishikura, T., Nitta, S. [The use of direct current in the local destruction of cancer tissues]. Gan To Kagaku Ryoho Apr. 1989; 16(4 Pt 2-2): 1412-1417.

Gravante et al., "Experimental Application of Electrolysis in the Treatment of Liver and Pancreatic Tumours: Principles, Preclinical and Clinical Observations and Future Perspectives," Elsevier Ltd., ScienceDirect, dated Dec. 7, 2009, 15 pages.

Dalziel et al., "Let-Go Currents and Voltages," Transactions of the American Institute of Electrical Engineers, Part II: Applications and Industry, 75(2): pp. 49-56, 1956.

PCT/US2018/062618, PCT International Search Report and Written Opinion dated Feb. 19, 2019, 7 pages.

Application and File history for U.S. Appl. No. 12/544,112, filed Aug. 19, 2009. Inventors: Fruland et al.

Application and File history for U.S. Appl. No. 14/969,889, filed Dec. 15, 2015. Inventors: Fruland et al.

Application and File history for U.S. Appl. No. 16/806,890, filed Mar. 2, 2020. Inventors: Fruland et al.

Application and File history for U.S. Appl. No. 12/544,119, filed Aug. 19, 2009. Inventors: Sundquist et al.

Application and File history for U.S. Appl. No. 12/544,127, filed Aug. 19, 2009. Inventors: Holtz et al.

Application and File history for U.S. Appl. No. 12/544,134, filed Aug. 19, 2009. Inventors: Nelson et al.

Application and File history for U.S. Appl. No. 15/455,358, filed Mar. 10, 2016. Inventors: Nelson et al.

Application and File history for U.S. Appl. No. 16/148,756, filed Oct. 1, 2018. Inventors: Nelson et al.

Application and File history for U.S. Appl. No. 16/287,551, filed Feb. 27, 2019. Inventors: Kroll et al.

\* cited by examiner

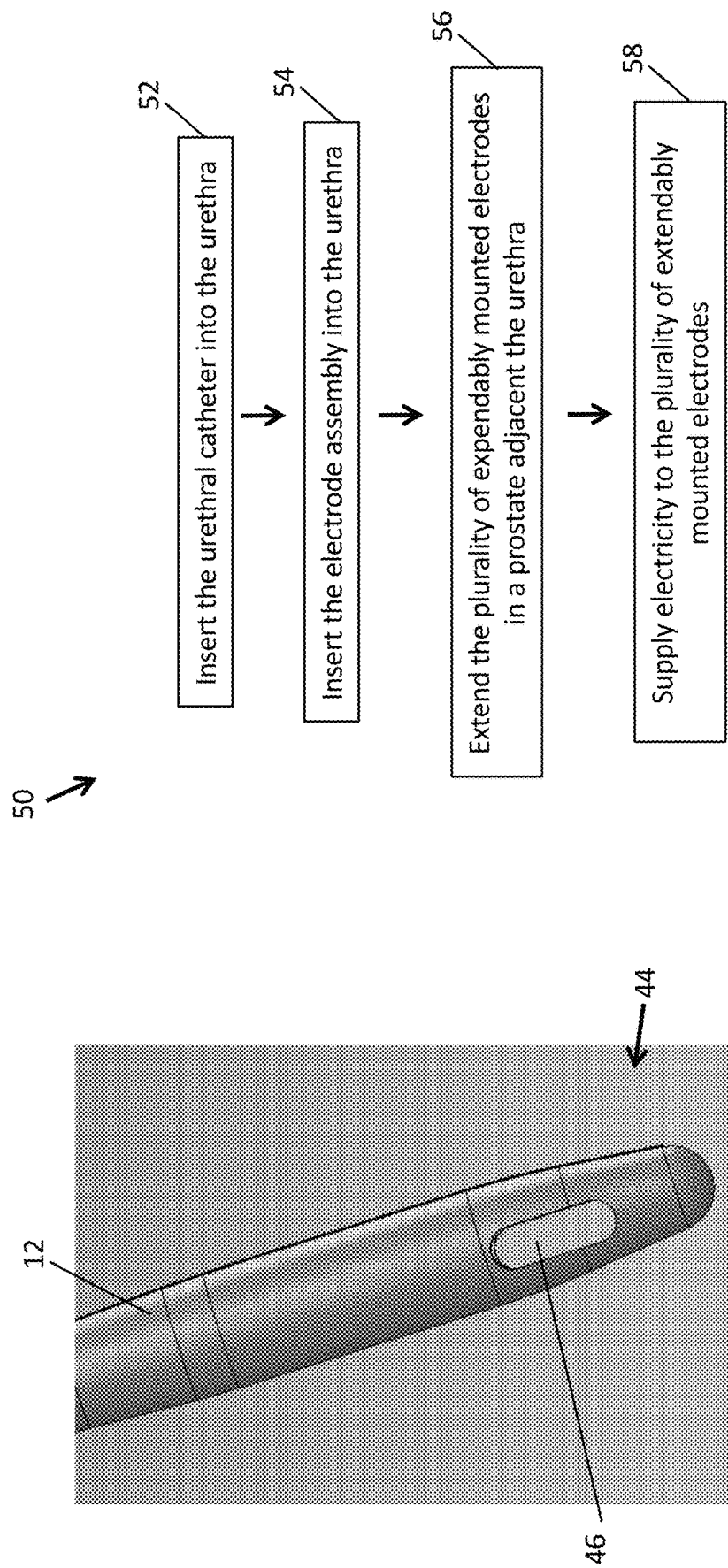

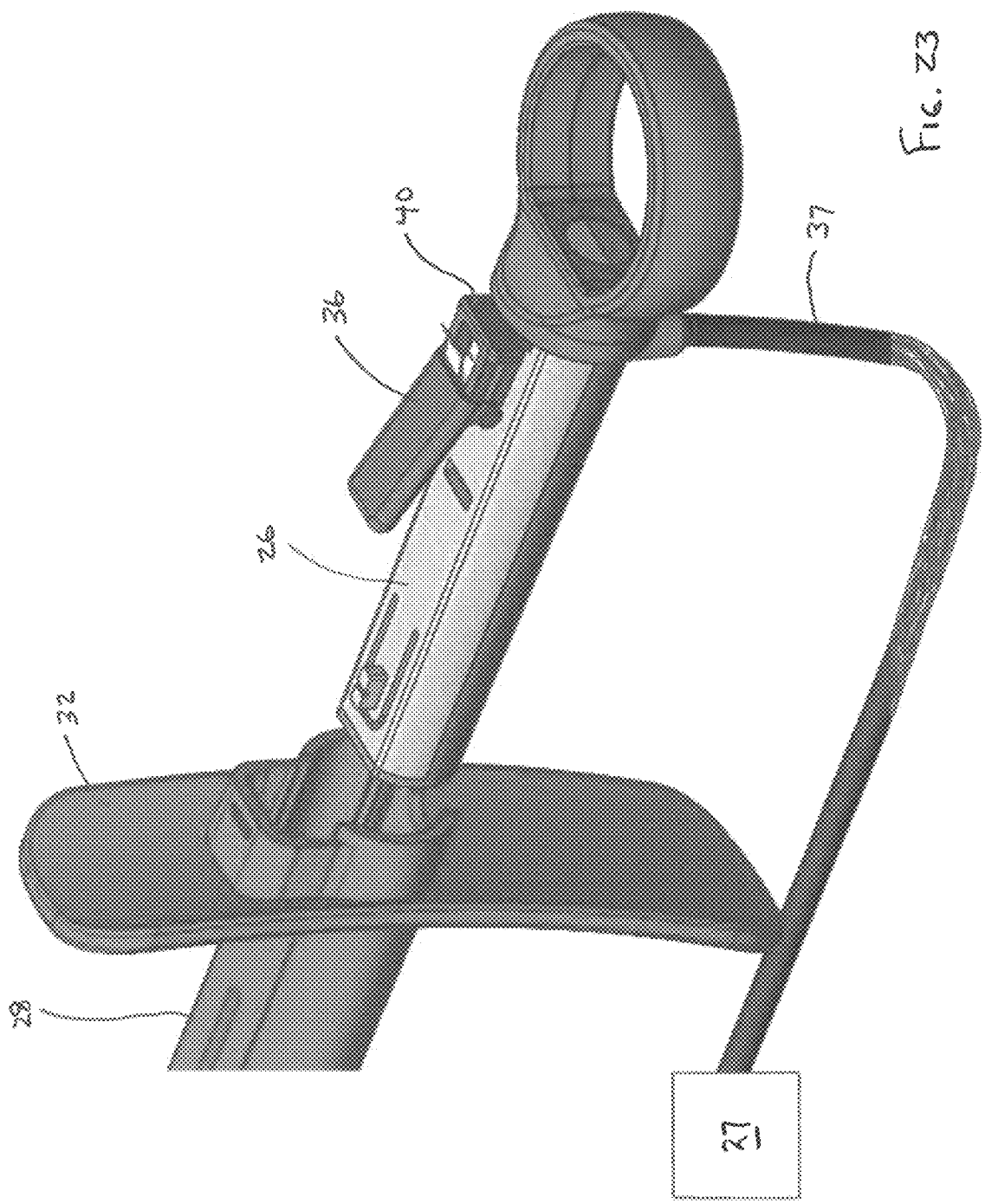

APPARATUS AND A METHOD FOR THE TREATMENT OF A PROSTATIC DISEASE

CROSS REFERENCE TO RELATED APPLICATION

This application claims the benefit of Australian Patent Publication No. 2017/904778 filed Nov. 27, 2017, which is hereby fully incorporated herein by reference.

TECHNICAL FIELD

The disclosure herein generally relates to an apparatus and a method for the treatment of a prostatic disease by transfer of electrical energy to a prostate in a body of a patient.

BACKGROUND

FIG. 1 illustrates a simplified view of the anatomy and location of a prostate 3, 4. A urethra 1 passes upwards through an urethrae membranaceae ("external sphincter muscle") 2, through the prostate 3, 4 which surrounds the urethra, and into a urinary bladder 5. The prostate 3, 4 comprises three lobes: two major lobes 3, 4 and a median lobe. The median lobe is located generally behind the major lobes 3, 4.

Diseases of the prostate include benign prostate enlargement, benign prostatic hyperplasia or hypotrophy ("BPH"), and prostate cancer. BHP is generally caused by enlargement of the 15 median lode of the prostate. BHP may cause the prostate 3, 4 to compress the adjacent urethra 1. Symptoms of BPH include frequent urination, reduced urine flow, lack of control of urination, painful urination, and bloody urination.

These very common prostatic diseases may be treated with pharmaceuticals, lifestyle changes, and ablation of prostate tissue. Ablative treatments include surgery, and induced necrosis of prostate tissue, and the subsequent removal of the necrotic tissue by bodily absorption or discharge via the urethra. Methods of inducing necrosis of prostate tissue include the heating and/or cooling of the prostate tissue, the introduction of toxic chemicals, and ultrasound. Examples of such methods include laser prostatectomy, interstitial laser coagulation, photosensitive vaporization of the prostate, holmium laser ablation of the prostate, holmium laser enucleation of the prostate, microware irradiation of the prostate, radiofrequency current heating, direct current ablation, and ultrasound treatment. Ablative and pharmaceutical treatments may have side effects including reduced libido, impotence, retrograde ejaculation, fatigue, dizziness, headache, and decreased blood pressure.

Examples of induced necrosis treatments for prostatic disease using chemical or cryo ablation are shown in U.S. Pat. Nos. 7,837,670 and 10,004,551, and PCT Publ. No. WO1997036632A1. Examples of induced necrosis treatments for prostatic disease using electrical thermal ablation are shown in U.S. Pat. Nos. 5,304,214, 5,370,675 and 6,524,270.

Minimally invasive treatments that utilize extendable electrodes configured to promote necrosis of prosthetic tissue via an electrolytic reaction have been developed as an alternative to other kinds of ablative treatments as shown, for example, in U.S. Pat. Nos. 9,211,155, 9,597,145, and 10,085,800, all of which are assigned to the assignee of the present disclosure.

Minimally invasive treatments of diseases of the prostate that offer at least one of less pain, faster recovery, lower costs, shorter treatment times, reduced treatment side effects, and reduced use of anesthesia and sedatives may be desirable. Improvements in the operation and control of existing minimally invasive treatments of diseases of the prostate may be desirable.

SUMMARY

Disclosed herein is an apparatus for the treatment of a prostatic disease. The apparatus comprises a urethral catheter for insertion into a urethra. The apparatus comprises an electrode assembly slidingly receivable within the urethral catheter. The electrode assembly comprises a plurality of extendably mounted electrodes for extension into a prostate adjacent the urethra. The plurality of extendably mounted electrodes are for electrolytic generation of at least one of a necrotizing base and a necrotizing acid within the prostate.

An embodiment comprises an inflatable balloon adjacent a distal end of the urethral catheter for inflation within a urinary bladder in fluid communication with the urethra, and another inflatable balloon disposed at a proximal end of the urethral bladder and in fluid communication therewith.

In an embodiment, each of the plurality of extendably mounted electrical electrodes are slidingly mounted and are attached at a proximal end thereof to an electrode propeller that is user actuatable. The electrode propeller may be linearly actuatable by the user.

An embodiment comprises a collar attached to a proximal end of the electrode assembly and rotationally fixed to the electrode propeller. The collar and the electrode propeller may be joined at a sliding keyed joint. A distal end of the urethral catheter may comprise a plurality of electrode passageways connecting an interior and exterior of thereof, and the urethral catheter and the electrode assembly are configured to engage with a predetermined rotational orientation to each other for alignment of the plurality of extendably mounted electrodes with the plurality of electrode passageways. The urethral catheter and the electrode assembly may be joined to form a sliding keyed joint. A flange may be attached to the collar, wherein the flange and the electrode propeller are cooperatively arranged for the flange to be received by a finger of a hand and the electrode propeller to be actuated by the thumb of the hand when the flange is so received.

An embodiment comprises a disengageable stop arrange to prevent actuation of the electrode propeller until disengaged.

In an embodiment, at least one of the electrode assembly and the urethral catheter comprise a fastener configured to fasten the electrode assembly to the urethral catheter when the electrode assembly is slidingly received within the urethral catheter.

An embodiment comprises a source of the electricity and a controller for the source of the electricity.

An embodiment comprises a monitor configured to generate electrical parameter information indicative of an electrical parameter associated with electricity supplied to the plurality of expendably mounted electrodes, wherein the controller is configured to control the electricity supplied to the plurality of expendably mounted electrodes depending on the electrical parameter information. The controller may be configured to change the electricity during the electrolytic generation of at least one of the necrotizing base and the necrotizing acid within the prostate. The controller may have a plurality of electrical modes for a plurality of prostates quality types.

In an embodiment, the electricity is a direct current.

In an embodiment, the plurality of extendably mounted electrodes comprises an electrode within an insulating sheath defining at least two uninsulated distal portions of the electrode.

In an embodiment, each of the plurality of extendably mounted electrodes comprise a rounded tip.

In an embodiment, each of the plurality of extendably mounted electrodes has a cruciform transverse section.

An embodiment comprises a chemical introducible by at least one of the plurality of electrodes into the prostate.

An embodiment defines a plurality of channels for each electrode for selective disposition of each electrode within the prostate.

In an embodiment, at least one of the plurality of extendably mounted electrodes is more extendable than at least another one of the plurality of extendable lengths.

In an embodiment, the urethral catheter is more flexible than the electrical assembly.

In an embodiment, the urethral catheter comprises a fixation element.

In an embodiment, the urethral catheter comprises a Foley catheter.

Disclosed herein is a method for treatment of a prostatic disease. The method comprises inserting a urethral catheter into a urethra. The method comprises inserting an electrode assembly into the urethra. The electrode assembly comprises a plurality of extendably mounted electrodes. The method comprises extending the plurality of extendably mounted electrodes into a prostate adjacent the urethra. The method comprises supplying electricity to the plurality of extendably mounted electrodes wherein at least one of a necrotizing base and a necrotizing acid is generated within the prostate.

In an embodiment, the electrode assembly is disposed within the urethral catheter during insertion of the urethral catheter into the urethra. Alternatively, the electrode assembly may be inserted into the urethral catheter so inserted into the urethra.

In an embodiment the urethral catheter is more flexible than the electrode assembly.

An embodiment comprises extending the plurality of electrodes into the prostate adjacent the urethra comprising a user actuating an electrode propeller attached to the plurality of electrodes to extend a plurality of tips of the plurality of electrodes out of the electrode assembly and into the prostate.

An embodiment comprises the step of rotationally fixing a collar attached to a proximal end of the electrode assembly to the electrode propeller.

An embodiment comprises the step of joining the electrode propeller and the collar to form a sliding keyed joint.

An embodiment comprises disengaging a stop arranged to prevent actuation of the electrode propeller to enable actuation of the electrode propeller.

An embodiment comprises the step of generating electrical parameter information indicative of electricity supplied to the plurality of extendably mounted electrodes, wherein the controller is configured to control the electricity supplied to the plurality of extendably mounted electrodes depending on the electrical parameter information.

An embodiment comprises the step of changing the electricity supplied to the plurality of extendably mounted electrodes during the electrolytic generation of at least one of the necrotizing base and the necrotizing acid.

An embodiment comprises the step of selecting one of a plurality of electricity supply modes, the plurality of electricity supply modes being for treatment of a plurality of prostate quality types.

An embodiment comprises the step of changing the disposition of at least one of the plurality of extendably mounted electrodes within the prostate and supplying electricity to the at least one of the plurality of extendably mounted electrodes.

An embodiment comprises the step of introducing a chemical to a volume of the prostate, wherein the chemical belongs to a group of chemicals comprising a chemical that counters at least one of the necrotizing acid and the necrotizing base, and a necrotizing chemical that reduces or increases the pH within the prostate.

An embodiment comprises the step of introducing the chemical into the prostate via a lumen in at least one of the plurality of electrodes.

An embodiment comprises using electromyography to detect a sphincter urethrae membranaceae adjacent the urethra and position the plurality of electrodes relative to the sphincter urethrae membranaceae.

An embodiment comprises inflating a first balloon attached to a distal end of the urethral catheter within a urinary bladder in fluid communication with the urethra, and a second balloon disposed adjacent a proximal end of the urethral catheter and in fluid communication with the first balloon.

An embodiment comprises introducing a fluid into a balloon attached to a distal end of the urethral catheter and disposed within a urinary bladder in fluid communication with the urethra, and monitoring the pressure of the fluid introduced into the balloon.

An embodiment comprises the step of reading an attached identification tag.

In an embodiment, the step of supplying the electricity to the plurality of extendably mounted electrodes comprises supplying electricity to the plurality of electrodes asynchronously.

An embodiment comprises the step of withdrawing the plurality of extendable electrodes from the prostate and extending another plurality of extendably mounted electrodes of another electrode assembly into the prostate at a different prostate position.

An embodiment comprises the step of activating a fixation element of the urethral catheter.

In an embodiment, the urethral catheter comprises a Foley catheter.

Disclosed herein is an apparatus for the treatment of a prostatic disease. The apparatus comprises an electrode assembly slidingly receivable within a urethral catheter, the electrode assembly comprising a plurality of extendably mounted electrodes for extension through urethral tissue and into a prostate, wherein the plurality of extendably mounted electrodes are for electrolytic generation of at least one of a necrotizing base and a necrotizing acid within the prostate.

In embodiments of an apparatus or method disclosed above, the plurality of extendably mounted 5 electrodes comprises at least on electrolytically corrodible electrode.

An urethral catheter comprising a distally attached inflatable balloon for inflation within a body and a proximally attached inflatable balloon in fluid communication with the distally attached inflatable balloon for disposition exterior of the body when the distally attached inflatable balloon is so inflated within the body.

Disclosed herein is an apparatus for the treatment of a prostatic disease. The apparatus comprises an electrode assembly slidingly receivable within a urethral catheter. The electrode assembly comprises a plurality of extendably mounted electrodes for extension through urethral tissue and into the prostate. The plurality of extendably mounted electrodes are for electrolytic generation of at least one of a necrotizing base and a necrotizing acid within the prostate.

Any of the various features of each of the above disclosures, and of the various features of the embodiments described below, can be combined as suitable and desired.

BRIEF DESCRIPTION OF THE FIGURES

The disclosure can be more completely understood in consideration of the following detailed description of various embodiments of the disclosure, in connection with the accompanying drawings, in which:

FIG. 9 shows a detail of a distal end of a urethral catheter of the apparatus of FIG. 1.

FIG. 10 shows a flow chart for an embodiment of a method for treatment of a prostatic disease that may be implemented using the apparatus of FIG. 2.

FIG. 23 is an exploded, partial perspective view depicting an electrode assembly handle, in accordance with an embodiment of the disclosure.

Figure 1:
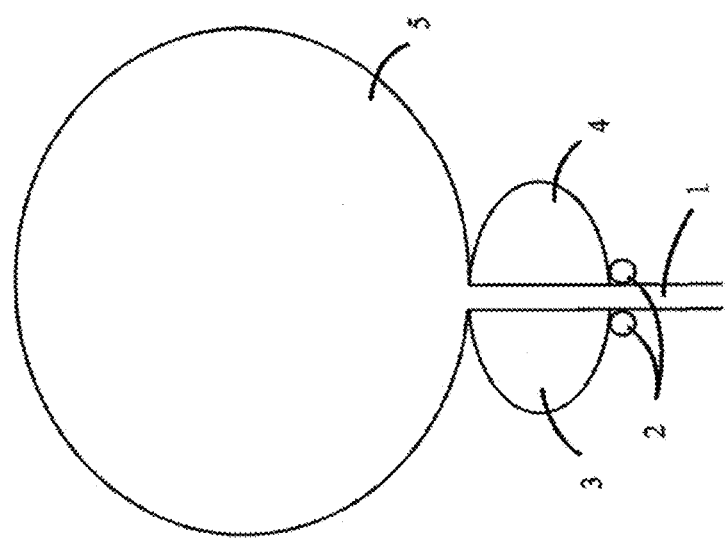
FIG. 1 illustrates a simplified view of the anatomy and location of a prostate.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DESCRIPTION OF EMBODIMENTS

Figure 4:
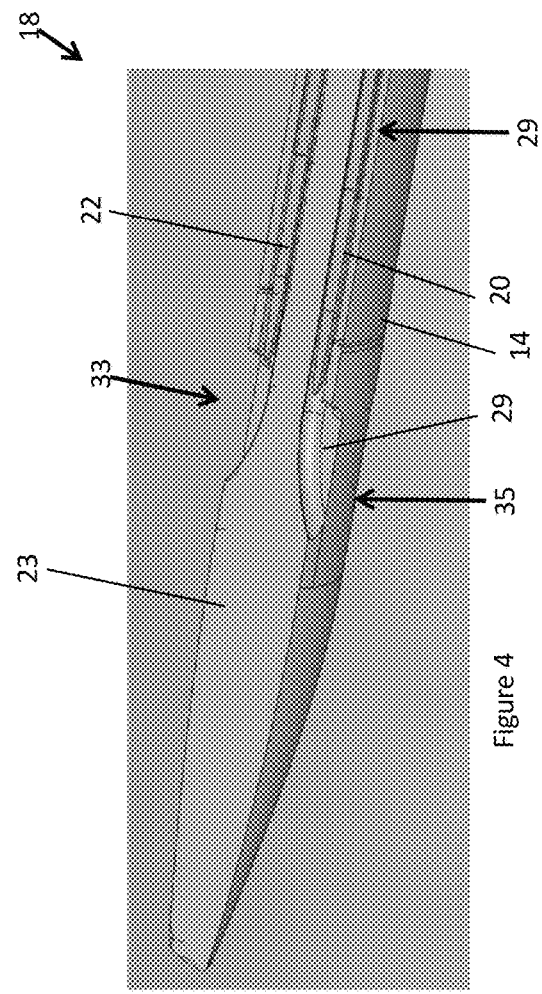
FIG. 4 shows a detail of a distal end of an electrode assembly of the apparatus of FIG. 2.
Figure 2:
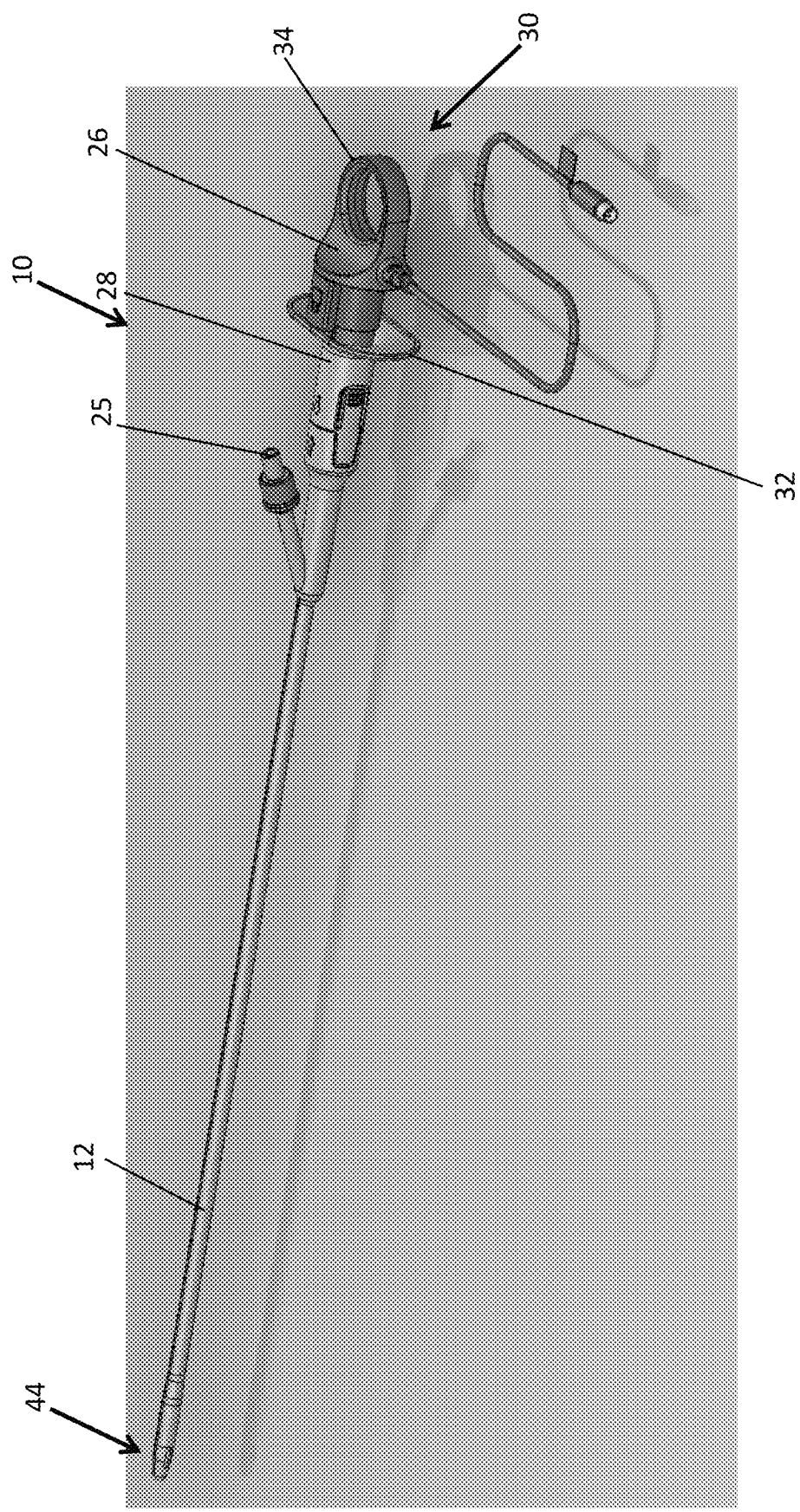
FIGS. 2 and 3 respectively show perspective and exploded views of an embodiment of an apparatus for the treatment of a prostatic disease
Figure 3:
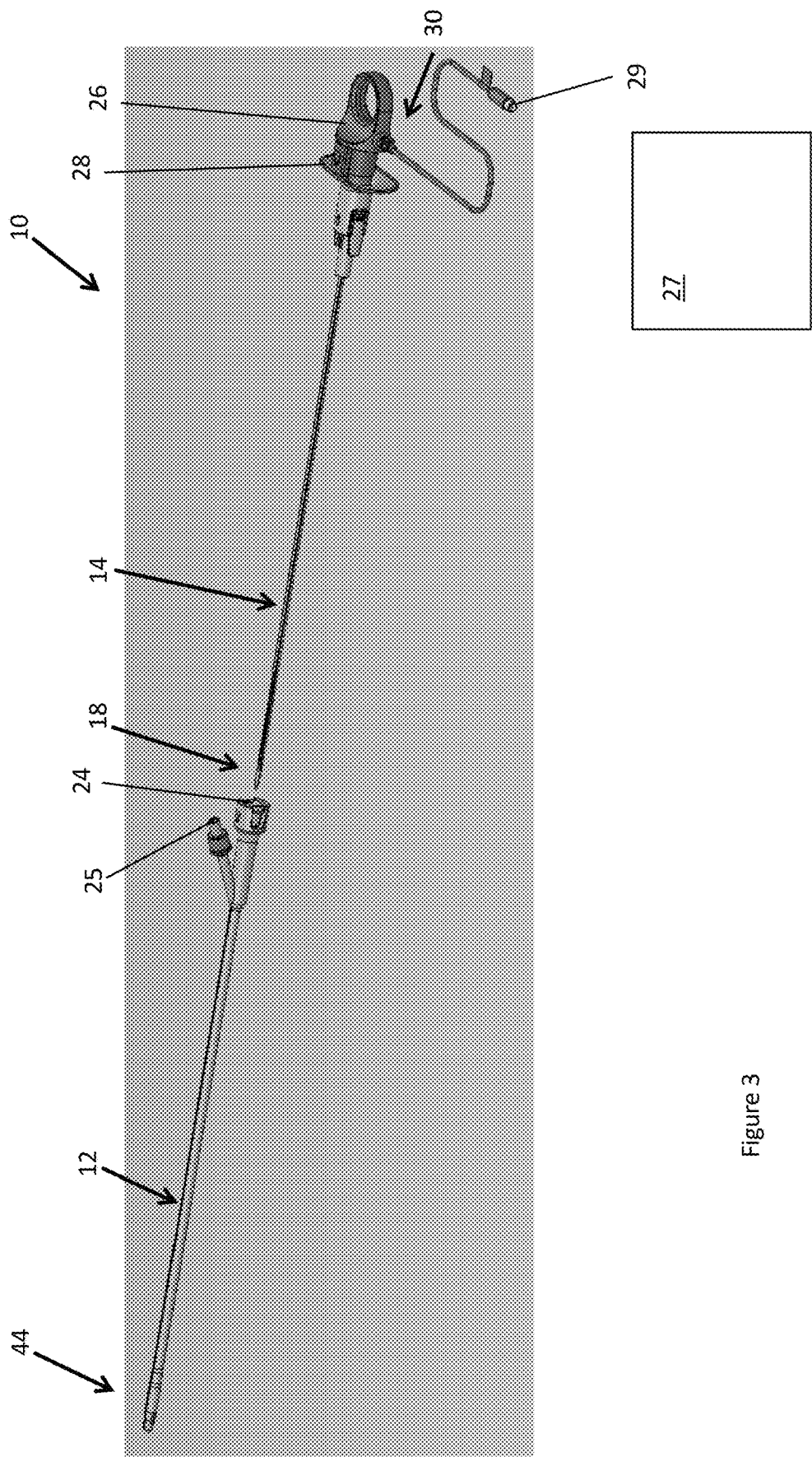
Figure 5:
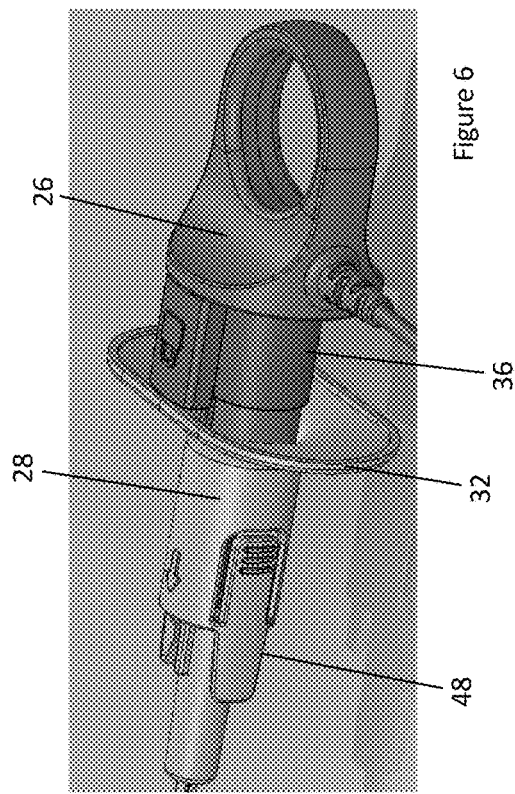
FIG. 5 shows a detail of a proximal end of a urethral catheter of the apparatus of FIG. 2.

FIGS. 2 and 3 respectively show perspective and exploded views of an embodiment of an apparatus for the treatment of a prostatic disease, the apparatus being generally indicated by the numeral 10. The apparatus 10 may be non-implantable. The apparatus 10 comprises a urethral catheter 12 in the form of a Foley catheter for insertion into a urethra 1. The apparatus 10 comprises an electrode assembly 14 slidingly receivable within the urethral catheter 12. FIG. 2 shows the electrode assembly 14 received within the urethral catheter 12. FIG. 4 shows a detail of the distal tip 18 of the electrode assembly 14, which is inserted into a proximal opening 24 of a lumen 31 of the urethral catheter 12. The proximal opening is best seen in FIG. 5. The electrode assembly 14 comprises a plurality of extendably mounted electrodes 20, 22 in the form of a memory alloy wire for extension into a prostate 3, 4 adjacent the urethra 1. The plurality of extendably mounted electrodes 20, 22 are for electrolytic generation of at least one of a necrotizing base and a necrotizing acid within the prostate 3, 4.

The plurality of electrodes may comprise, for example, a pair of electrodes 20, 22, or multiple pairs of electrodes. One electrolytic reaction that may occur in the prostate is the electrolysis of water, whereby a necrotizing base (OH−) may be generated at an electrode that is a cathode, and a necrotizing acid (H+) may be generated at an electrode that is an anode. The necrotizing base and necrotizing acid may each cause necrosis of prostatic tissue to form a necrotic volume of prostatic tissue, which in some embodiments is predetermined prior to treatment. The necrotic prostate tissue is absorbed by the body or excreted via the urethra, leaving a void and so reducing the prostate volume, which may reduce the symptoms of BPH or the size of a tumor.

In use, a portion of the catheter comprising proximal opening 24 and port 25 remain outside of the body. The urethral catheter comprises a fixation element in the form of an inflatable balloon adjacent a distal end of thereof, to fix the catheter in a treatment position. The inflatable balloon is for inflation within a urinary bladder in fluid communication with the urethra, which aids in the retention of the urethral catheter within the urethra. The balloon may be inflated with saline, air, or generally any suitable form of fluid. The saline or air may be introduced via a urethral catheter inflation port 25, which is in fluid communication with the balloon via a fluid conduit in the form of another lumen of the urethral catheter 12.

The urethral catheter 12 comprises another inflatable balloon disposed adjacent a proximal end of the urethral catheter 12 and in fluid communication therewith. The other balloon is disposed such that it is external of the urethra when the balloon is inflated within the bladder. The other balloon is a visual indicator of the inflation state of the balloon in the bladder, and deflation of the other balloon is indicative of a potentially dangerous state wherein the urethral catheter may slip and so cause the extended electrodes to score the urethral epithelium. Alternatively, embodiments may comprise a pressure meter in fluid communication with the balloon to monitor the pressure of the fluid within the balloon. The pressure gauge may generate a fluid pressure signal that may trigger an alarm, for example, or stop the supply of electricity when fluid pressure signal is indicative of balloon deflation.

Figure 6:
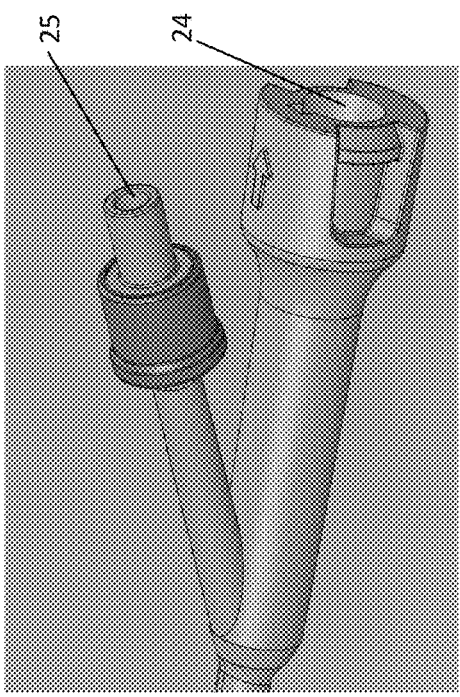
FIGS. 6 and 7 show details of a proximal end of the electrode assembly of FIG. 4, with and without a disengageable stop respectively.

Each of the plurality of extendably mounted electrical electrodes 20, 22 are slidingly mounted in channels 29 of the electrode assembly 14, that turn outwardly at the distal end thereof. The plurality of extendably mounted electrical electrodes 20, 22 are attached at a proximal end thereof to an electrode propeller 26 in the form of a handle, or generally any user engageable form including but not limited to a knob or plunger, that is user actuatable. The electrode propeller 26 is linearly actuatable by the user, whereby the separation of the electrode propeller 26 and distal end of the electrode assembly 14 is reduced. A collar 28 is attached to a proximal end 30 of the electrode assembly 14. The collar may be integral or differentiated. A flange 32 can be distally disposed and attached to the collar 28. The flange 32 and the electrode propeller 26 are cooperatively arranged for the flange 32 to be received by a finger of a hand and the electrode propeller 26 to be actuated by the thumb of the hand when the flange 28 is so received. The thumb may be inserted in a ring 34 of the electrode propeller 26. As shown in FIG. 6, a disengageable stop 36 is arranged to prevent actuation of the electrode propeller 26 until disengaged, as shown in FIG. 7.

Figure 8:
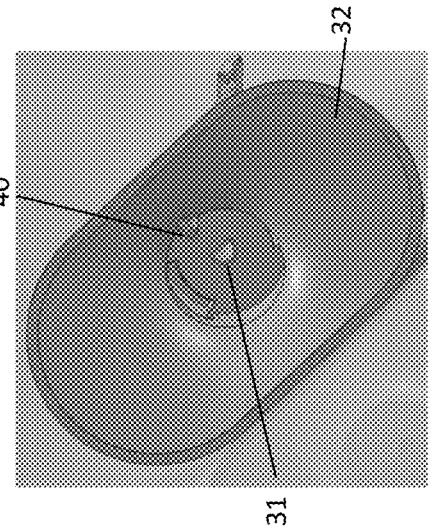
FIG. 8 shows a detail of a flange shown in FIGS. 6 and 7.
Figure 7:
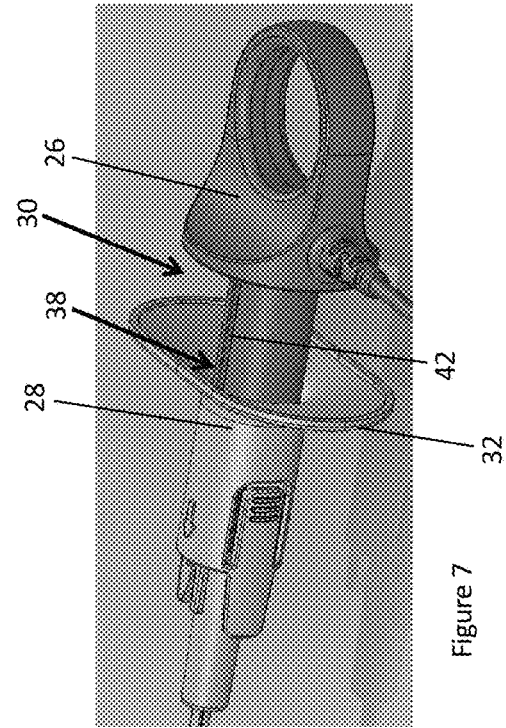

As best understood with reference to FIGS. 7 and 8, the collar 28 is rotationally fixed to the electrode propeller 26. The collar 28 and the distal end 30 of the electrode assembly, in this embodiment the electrode propeller 28, are joined by a sliding keyed joint 38. One of the distal end 30 of the electrode assembly and the collar 28 comprise a key 40 in the form of a longitudinal rib, and the other of the distal end 30 of the electrode assembly and the collar 28 comprises a keyway 42 in the form of a longitudinal groove. The key 40 is received within the keyway 42 for longitudinal sliding movement between the collar 28 and electrode propeller 26, while fixing their relative rotational orientation around a common axis.

As best seen in FIG. 9, a distal end 44 of the urethral catheter 12 comprises a plurality of electrode passageways 46 connecting the lumen to the exterior. The present embodiment has two electrode passageways opposite each other for passage of the electrodes 20, 22. The urethral catheter 12 and the electrode assembly 14 are configured to engage with a predetermined rotational orientation to each other for alignment of the plurality of extendably mounted electrodes 20, 22 with the plurality of electrode passageways.

As seen in FIG. 4, the electrode assembly 18 has a "D" shaped lateral section that is received by the lumen 31 having a complementary "D" shape, as seen in FIG. 8. Generally, the electrode assembly and the lumen 31 may generally have any suitable interlocking cross sectional shapes, for example hexagonal, 10 square, or an arbitrary irregular shape. The urethral catheter 12 and the electrode assembly 14 can be joined to form a sliding keyed joint, as shown in FIG. 2.

Also shown in FIG. 4 is an attached electrode assembly tip 23. The attachment may be by an ultrasonic, RF wield, or with adhesive. The assembly tip 23 has a scoop to assist in insertion. The tip may be replaced with another tip having different electrode port 33, 35 positions.

At least one of the electrode assembly 14 and the urethral catheter 12 may, as in the present embodiment, comprise a fastener 48 in the form of a clip configured to fasten the electrode assembly 14 to the urethral catheter 12 when the electrode assembly is slidingly received within the urethral catheter. This may prevent accidental withdrawal of the electrodes during a procedure, for example.

Embodiments may comprise a source 27 of the electricity, which is generally but not necessarily in the form of a direct current, and a controller for the source of the electricity. The power supplied to the electrodes is low compared to prior methods for treating BPH. The power supplied may be of the order of milliwatts, for example in the range of 20 to 3200 mW of power per electrode pair. The power typically used for each electrode pair is between approximately 190 mW (25 mA into a 300 ohm tissue impedance) to 1600 mW (40 mA into a 1000 ohm tissue impedance). A common impedance level seen in tissue is 400 ohms, and treating with 50 mA equates to a required power output of 1000 mW. This relatively low power results in insignificant heat transfer between the apparatus 10 and body tissues. This reduces or eliminates pain and discomfort from the heating of surrounding tissues during treatment that are experienced with thermal technologies utilizing significantly higher power. It also reduces or eliminates scarring and long healing times associated with a thermal wound. RF and microwave technologies using thermal energies to create necrosis in soft tissue often have power ranges between 15 and 75 W. The amount of power delivered by a thermal ablation system is not based directly on the measurement of the power delivered, but is based on the temperature measurement resulting from the power delivered. In contrast, the amount of charge delivered by the present embodiment is based directly on the measurement of the charge delivered, allowing for more precise control of the size of the necrotic zones.

The apparatus 10 may have an electrical connector 37 in electrical communication with the plurality of extendably mounted electrodes for making an electrical connection with the source 27. The ablation of the prostate tissue is non-thermal, and a form of direct current ablation. Some embodiments may comprise a monitor configured to generate electrical parameter information indicative of an electrical parameter associated with electricity supplied to the plurality of expendably mounted electrodes. The controller is configured to control the electricity supplied to the plurality of expendably mounted electrodes depending on the electrical parameter information. For example, the monitor may measure the impedance experienced by the current in the form of a DC current that is supplied to the electrodes, the current flowing from one of the plurality of electrodes 20, 22 to another one of the plurality of electrodes 20, 22.

Gas bubbles in the form of hydrogen and oxygen, for example, may be generated in the prostate tissue adjacent the plurality of extendably mounted electrodes during the electrolytic generation of at least one of a necrotizing base and a necrotizing acid within the prostate 3, 4, which generally increases the impedance of the current that may flow and decrease the rate at which the necrotizing acid and/or base are generated. Chlorine gas may saturate the cathode surface. The tissue may dehydrate at the anode. To counter the increase in impedance, the controller is in this but not necessarily in all embodiments configured to change the electricity during the electrolytic generation of at least one of the necrotizing base and the necrotizing acid within the prostate. For example, the current and/or voltage may be reduced or increased so that the rate of gas generation is approximately equal to the rate of gas absorption by the prostate, which manifests in a stable impendence. Alternatively, the controller may turn off the current to allow gas to be absorbed, and after the gas has been absorbed turn on the current. In the present embodiment, the controller reduces and/or turns off the supplied current when the impedance satisfies a first impendence condition, for example when the impedance is equal to or greater than a first impedance condition. The impedance may then drop as the gas is absorbed. When the measured impedance satisfies a second impedance condition, for example the impedance is equal to or less than a second threshold impedance, the controller increases and/or turns on the supplied current. In another embodiment, the controller may in response to determined impendence cause the supplied current to dither, for example oscillate, or fluctuate the current. The electricity supplied to the electrodes may be modulated to prevent the build-up of gas bubbles.

Electricity may be supplied to the plurality of electrodes asynchronously, for example first to one pair of electrodes, and then to another pair of electrodes. Switching the supply of electricity to the other pair of electrodes may result in a reduction in impedance because of the absence of gas bubbles thereat. The controller has a plurality of electrical modes for a plurality of prostates quality types. For example, the prostate may have different impedance depending of its age, or ability to absorb generated gases. MM or ultrasound imagining may be used to determine the prostate quality type. The different modes may have different temporal electrical profiles.

The plurality of extendably mounted electrodes 20, 22 may in some embodiments comprise an electrode within an insulating sheath defining at least two uninsulated distal portions of the electrode. The uninsulated distal portions each act as a site for electrolysis, and may assist in reduction of gas build-up, or other sources of impedance. The sheath may take the form of a film, a membrane, a tube or generally any suitable form. This may allow skipping of electrolysis between uninsulated distal portions, the skipping being in response to variations in impedance between the uninsulated distal portions.

Each of the plurality of extendably mounted electrodes comprises a rounded or ground tip that is coated with platinum. This may reduce the incidence of scoring of the urethral epithelium when the electrodes are withdrawn. The electrodes are insulated with a polyimide membrane or generally any suitable form intermediate the distal and proximal ends. In an alternative embodiment, each of the plurality of extendably mounted electrodes has a cruciform transverse section. This may maximize the surface area of the extendably mounted electrodes and enable greater current delivery for a given voltage, which may assist in minimizing gas generation in the tissue.

Embodiments may comprise a chemical introducible by at least one of the plurality of electrodes into the prostate. At least one of the electrodes may comprise a lumen connected to the exterior for delivery of the chemical within the prostate. The chemical may alternatively be attached to the surface of the at least one electrode, and may be a chemical coating on the at least one electrode. The chemical generally belongs to a group of chemicals comprising a chemical that counters at least one of the necrotizing acid and the necrotizing base, and a necrotizing chemical that reduces or increases the pH within the prostate. Alternatively or additionally, the chemicals may counter the prostates natural pH buffer. The chemical may start acting before sufficient necrotizing base or acid has been electrolytically generated. For example, the chemical may comprise an acid salt coating or a basic salt coating, which may cause necrosis before sufficient necrotizing acid and/or necrotizing base has been electrolytically generated. The chemical may slough off when electricity is supplied to the at least one electrode, for example. The chemicals may be deposited for treatment of a first volume, and then the electrodes disposed elsewhere for treatment of a second volume by electrolytically generating necrotizing acid or base. The shape of the treated volume may be influenced by the introduction of the chemical.

A saline solution or saline gel may be introduced into a volume where ablation of tissue is not desired. In some embodiments, a saline solution with a pH of 7 may be provided adjacent to a treatment volume. This substantially prevents the necrotizing acid and base from advancing into a volume where ablation of tissue is not desired. The neutral pH of the saline dilutes the advancing acidic and basic gradient to prevent necrosis in irrigated volumes. The saline solution may be delivered by any suitable method. For example, saline may be introduced into a body lumen where preservation is desired, such as the urethra, through the therapy delivery catheter or through a separate dedicated irrigation catheter.

In some embodiments, at least one of the plurality of extendably mounted electrodes is more extendable than at least another one of the plurality of extendable lengths. The more extendable electrode may be moved during treatment when the impendence exceeds a threshold value.

The plurality of extendably mounted electrodes comprise Titanium-Nickel alloy (Nitinol) and may be coated with a corrosion resistant coating in the form of, for example, platinum. The electrodes may be configured to be atraumatic. When extended, the tips of the extendably mounted electrodes penetrate the urethra wall and then penetrate the prostate. The electrode tips may be sufficiently sharp to penetrate the urethra wall.

In an embodiment, at least one of the plurality of extendably mounted electrodes is electrolytically corrodible. An electrolytically corrodible electrode is corroded by the electrolytic process, resulting in the deposition of favorable or at least neutral ions in the ablated prostate area. Favorable ions may include silver ions that are anti-infective, magnesium ions, or iron ions. Electrode material that is cheaper than Platinum may be used.

FIG. 10 shows a flow chart 50 for steps of an embodiment of a method for the treatment of a prostatic disease that can be performed using the apparatus 10. The method comprises the step 52 of inserting the urethral catheter 12 into a urethra 1. The method comprises the step 54 of inserting the electrode assembly 14 into the urethra. The method comprises the step 56 of extending the plurality of extendably mounted electrodes 20, 22 into a prostate adjacent the urethra 1. The method comprises the step 58 of supplying electricity to the plurality of extendably mounted electrodes 20, 22. One of a necrotizing base and a necrotizing acid is electrolytically generated within the prostate when a current flows from one electrode to another electrode via the prostate.

In the present embodiment, the electrode assembly 14 is disposed within the urethral catheter 12 during insertion of the urethral catheter 12 into the urethra 1. In another embodiment, however, the electrode assembly 14 is inserted into the urethral catheter 12 subsequent to insertion of the urethral catheter 12 into the urethra 1. The urethral catheter 12 is more flexible than the electrode assembly 14. The urethral catheter 12 may comprise, for example, silicone. It may be easier to insert the urethral catheter first. Once inserted, the urethral catheter 12 acts as a guide for the electrode assembly 12 when inserted, and protects the urethra 1 from, for example, accidental puncture by the relatively less flexible electrode assembly.

In some embodiments for treatment of BPH, the cathode may be placed proximate the bladder neck or base of the prostate. A cathode so placed creates a large area of necrosis with less relative variation. The area closest to the bladder neck in the prostate is responsible for the greatest contribution to lower urinary tract symptoms due to BPH. The anode may be placed closer to the verumontanum. Another embodiment includes placing the cathodes in the lateral posterior quadrant of the tissue relative to the urethra and placing the anodes in the lateral or lateral anterior quadrant of the tissue relative to the urethra. A treatment zone forms around each of the electrodes and diffuses out generally passively. Thus, the electrodes may be placed in the tissue relative to each other such that the treatment zones overlap and coalesce.

After treatment, the electrode assembly 14 may be removed and the urethral catheter retained to assist in removal of urine from the urinary bladder 5 until at least one of, for example, the urethra is healed, inflammation has decreases, and swelling has decreased.

An embodiment comprises the step of changing the disposition of at least one of the plurality of extendably mounted electrodes within the prostate. Electricity is supplied to the at least one of the plurality of extendably mounted electrodes subsequent to the changing of its disposition. For example, the plurality of electrodes may be partially withdrawn or extended further. The electrodes may be fully withdrawn, the urethral catheter partially withdrawn or inserted deeper, and the electrodes extended to extend into a new site within the prostate. Different sites may be treated, or a new site with little or no generated gas may be found.

Electromyography may be used to detect the sphincter urethrae membranaceae ("external sphincter muscle") 2 adjacent the urethra 1 and prostate, and position the plurality of electrodes relative to the external urethral sphincter muscle. This may result is better positioning of the electrodes.

The plurality of expendably mounted electrodes may be withdrawn from the prostate, and another plurality of extendably mounted electrodes of another electrode assembly may be extended into the prostate at different prostate position. The treated volume may be increased, or a new volume with less impedance or no gas bubbles may, which may reduce treatment time.

An attached identification tag may be read. In the present but not all embodiments, the identification tag may be in the form of a radio frequency identification tag; however other types of identification tags may be used. The identity information read from the identification tag may be associated with procedure parameter information, commercial surveillance information, adverse event information for recall for example. The association may be within a computer data store, for example, that has received the information to be associated via a computer network.

In an embodiment, the electrical assembly comprises a sensing electrode. The sensing electrode is used to confirm that the electrodes are fully retracted in the apparatus 10. The impendence between each of the extendably mounted electrodes and the sensor electrode is determined, and a signal generated indicative of the extension state of at least one of the plurality of extendably mounded electrodes. The impedance between each of the retractably mounted electrodes and the sensor electrode is generally lower when the extendably mounted electrodes are withdrawn. The monitor may generate the signal when the impedance between each of the retractably mounted electrodes and the sensor electrode is less than a threshold—to indicated that the electrodes are withdrawn and it is safe to remove the apparatus from the urethra—or is greater than a threshold to indicate that at least one of the extendably mounted electrodes is extended and it is not safe to remove the electrode.

Figure 11:
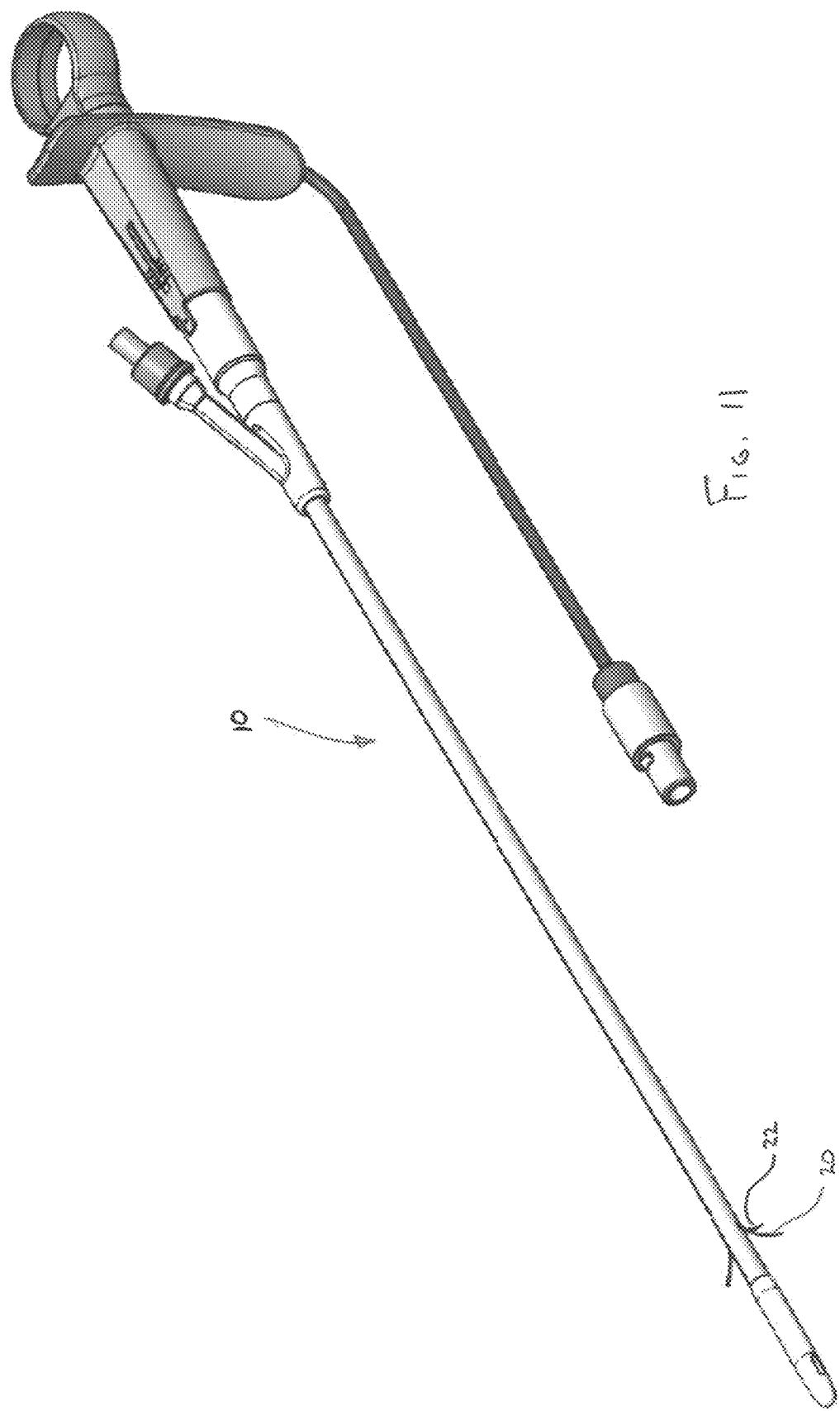
FIG. 11 is a perspective view depicting an apparatus for the treatment of a prostatic disease, in accordance with another embodiment of the disclosure.
Figure 12:
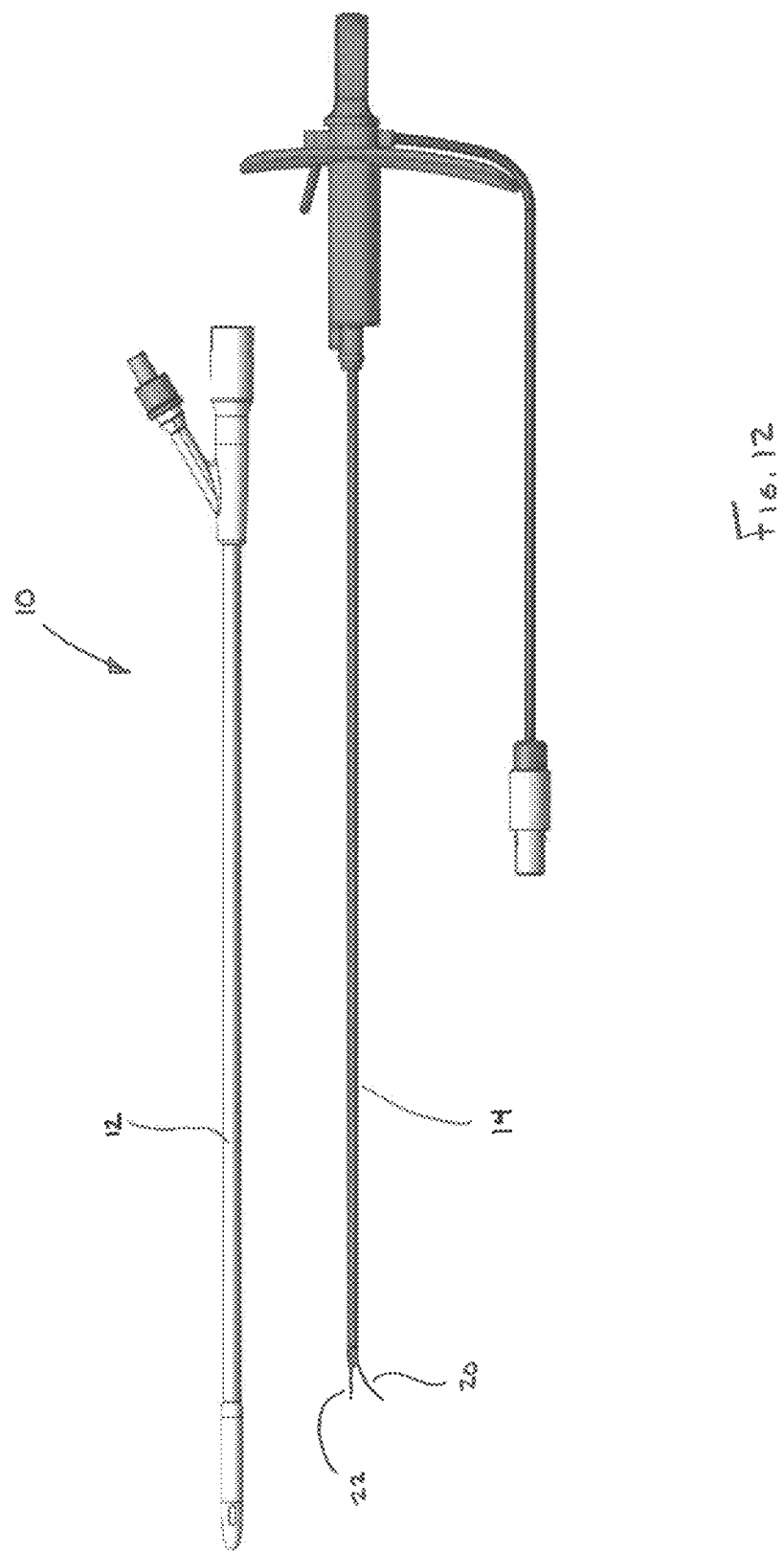
FIG. 12 is an exploded view depicting the apparatus of FIG. 11.

FIGS. 11 and 12 respectively show perspective and exploded views of another embodiment of an apparatus 10 for treatment of a prostatic disease. The apparatus 10 comprises a urethral catheter 12, and an electrode assembly 14 slidably received within the urethral catheter 12. FIG. 11 shows the electrode assembly 14 received within the urethral catheter 12.

Figure 13:
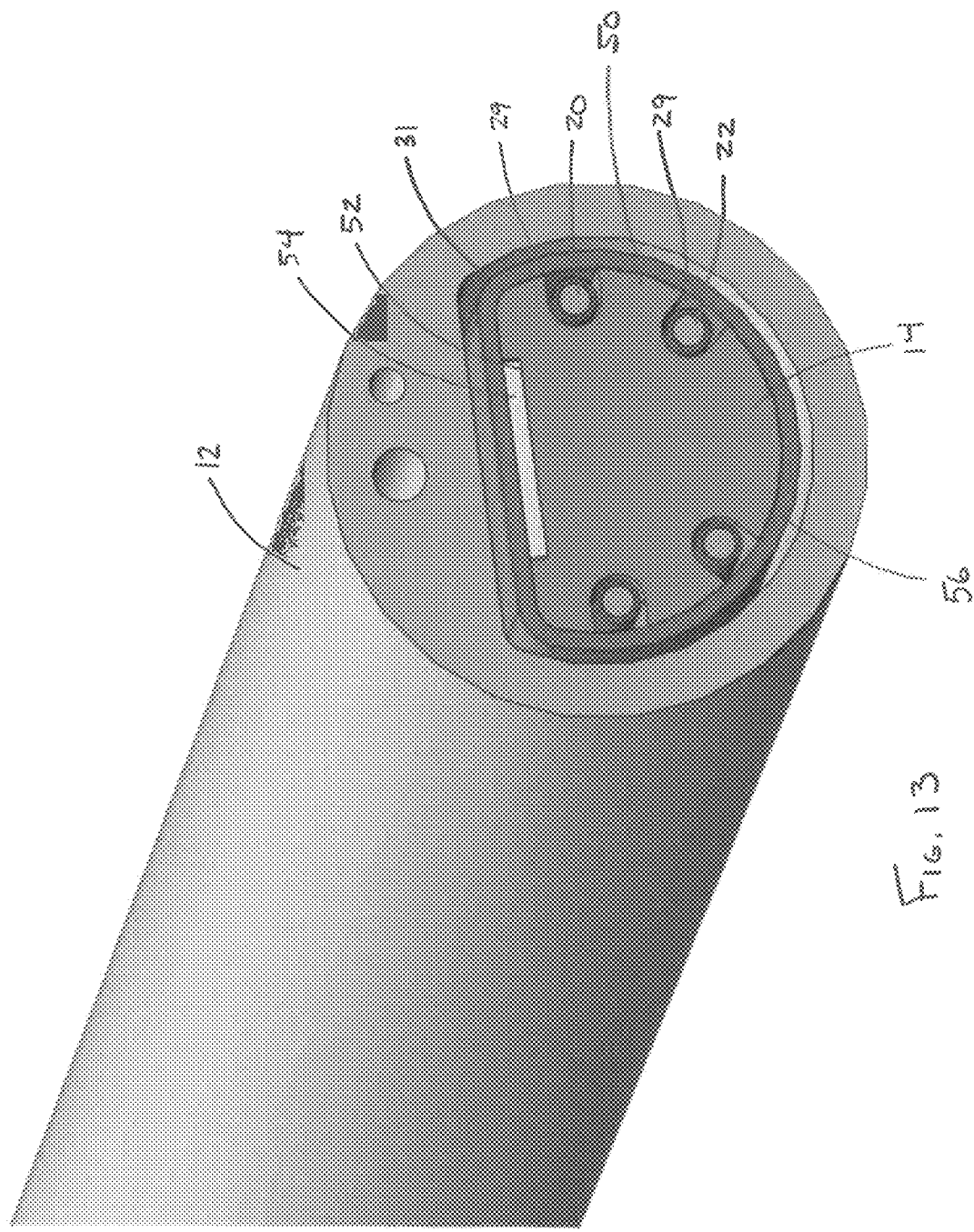
FIG. 13 is a cross sectional view depicting an electrode assembly slidably received within a urethral catheter, in accordance with an embodiment of the disclosure.

The urethral catheter 12 can include a catheter wall extending between a distal end 44 and a proximal opening 24 defining a lumen 31 therebetween. The urethral catheter 12 and the electrode assembly 14 are configured to slidably engage with one another via a predetermined rotational orientation to ensure proper alignment. To facilitate the predetermined rotational orientation, the electrode assembly 14 and the lumen 31 can generally have any suitable interlocking cross-sectional shape, for example, triangular, square, polygonal, or an arbitrary irregular shape. For example, as shown in FIG. 13, the electrode assembly 14 can have a "D" shaped lateral section that is received by a complementary "D" shaped lumen 31 of the catheter 12.

Figure 14:
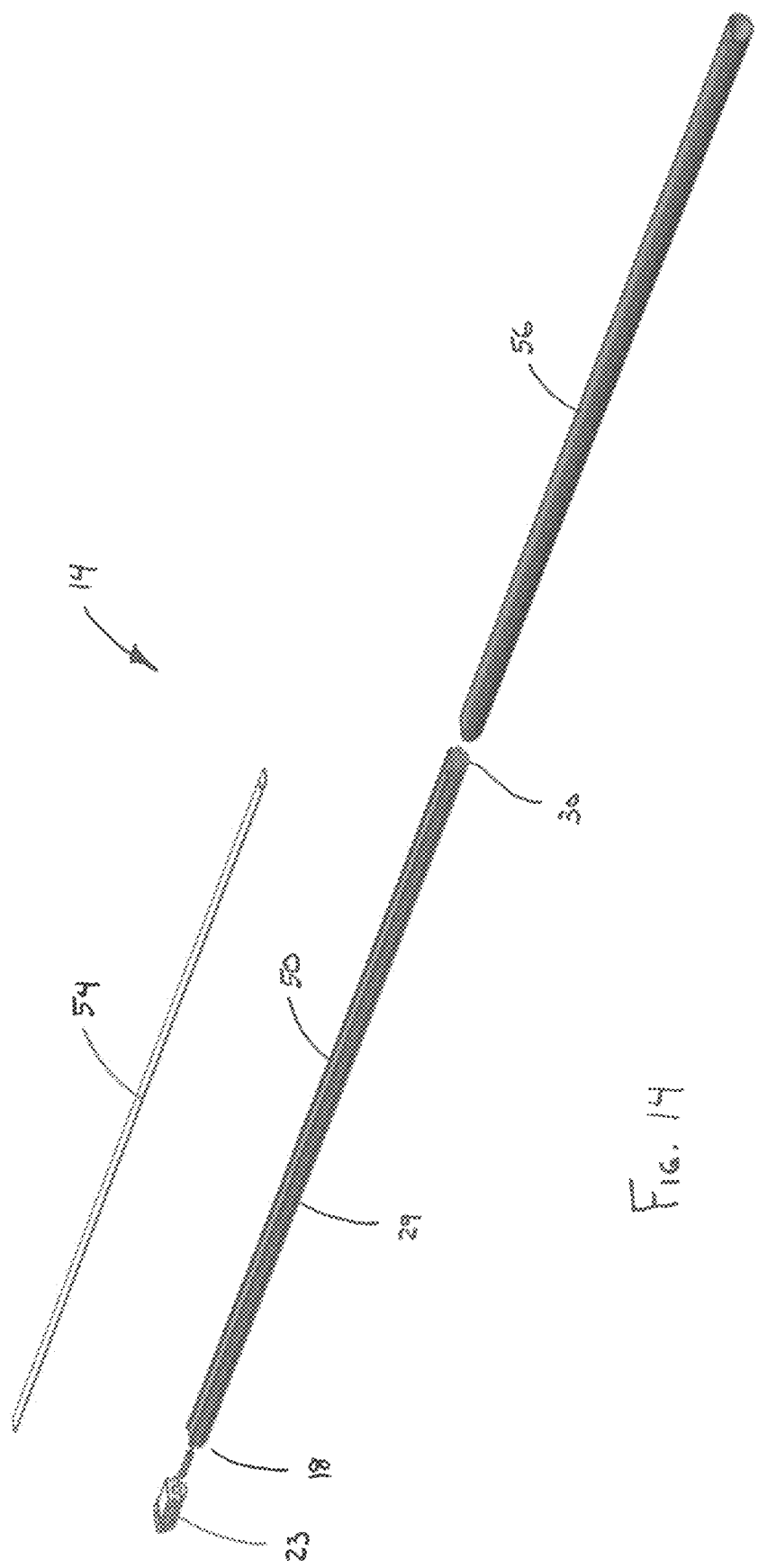
FIG. 14 is an exploded view depicting an electrode assembly, in accordance with an embodiment of the disclosure.

As shown in FIG. 14, the electrode assembly 14 can include an elongated member or shaft 50 extending between a distal tip 18 and a proximal end 30. The shaft 50 can define a plurality of channels 29 shaped and sized to accommodate a plurality of extendably electrodes 20, 22 therein. An electrode tip 23 can be operably coupled to the distal end 18 of the shaft 50.

Figure 15:
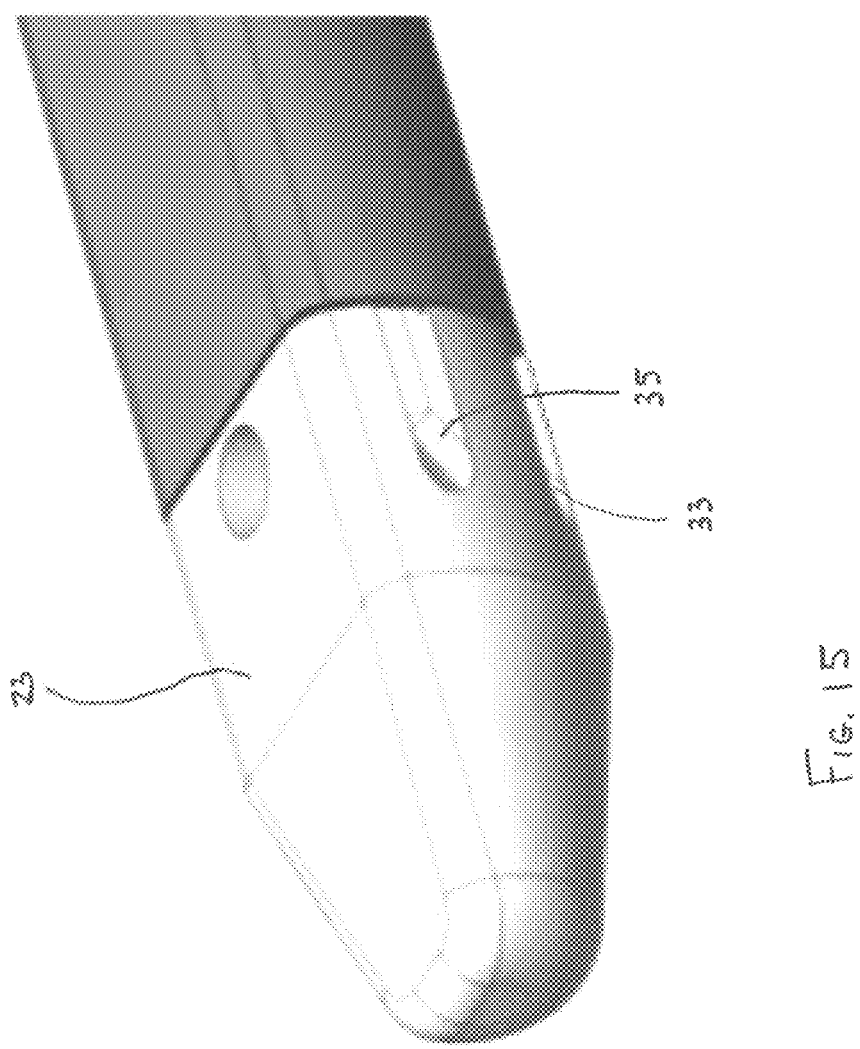
FIG. 15 is a partial, perspective view depicting an electrode tip of an electrode assembly, in accordance with an embodiment of the disclosure.

As shown in FIG. 15, the electrode tip 23 can define a plurality of electrode ports 33, 35 configured to guide the electrodes 20, 22 as they are extended out of the electrode assembly 14 and into surrounding prostatic tissue. In some embodiments, a user may choose from a variety of interchangeable electrode tips 23, which can be selectively coupled to the shaft 50. Various embodiments of electrode tips 23 can present different scoops or tapers and/or different electrode port 33, 35 configurations to accommodate a variety of patient conditions.

The shaft 50 can further define an anti-torsion strip channel 52, in which an anti-torsion strip 54 can reside. An over jacket 56 can be configured to at least partially surround the shaft 50, thereby encouraging the electrodes 20, 22 and anti-torsion strip 54 to remain within the respective channels 29, 52.

Figure 16:
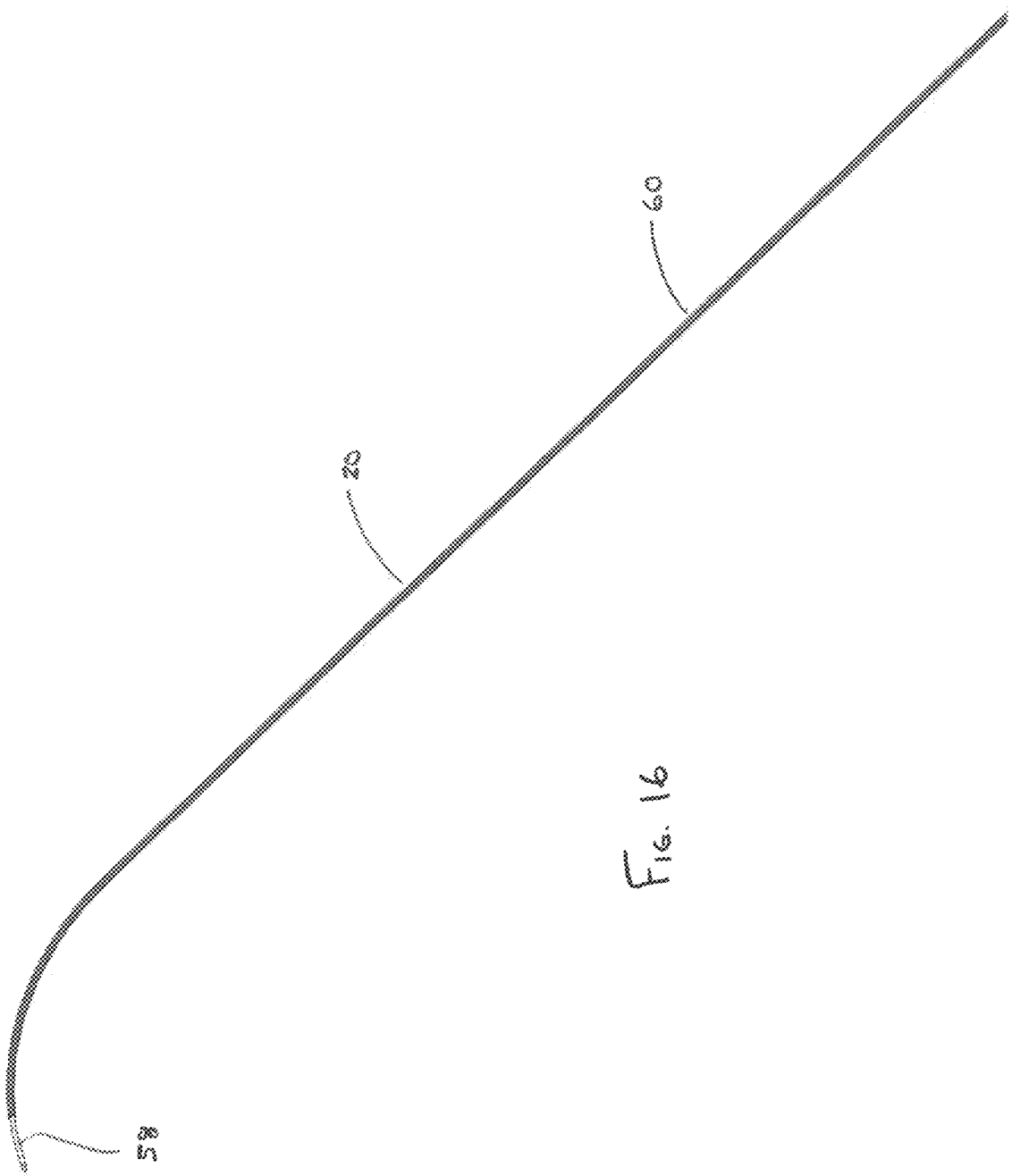
FIG. 16 is a partial, perspective view depicting an electrode, in accordance with an embodiment of the disclosure.
Figure 17:
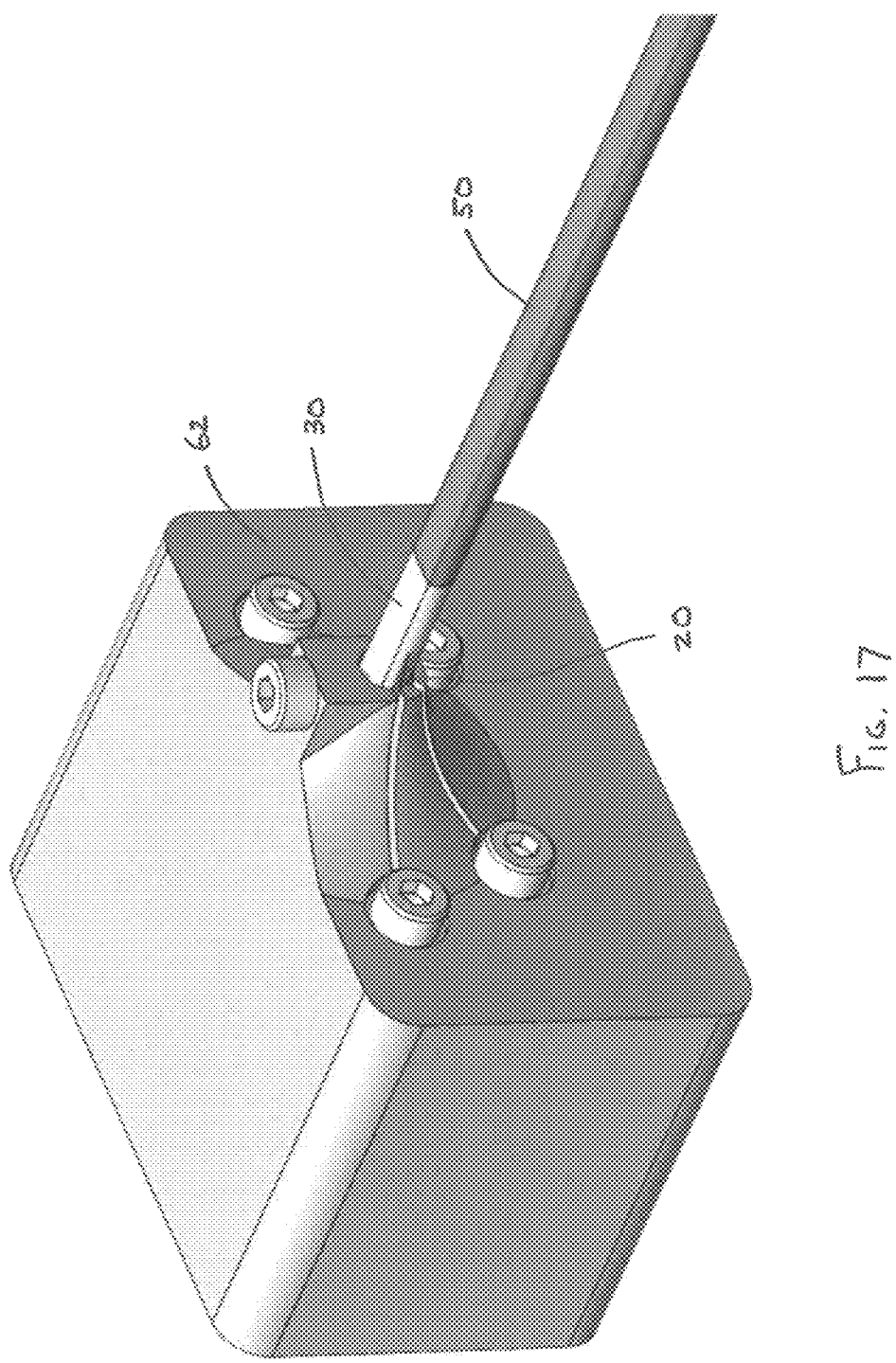
FIG. 17 is a partial, perspective view depicting a connection of an electrode assembly to an assembly fixture, in accordance with an embodiment of the disclosure.

Each of the plurality of extendable mounted electrodes 20, 22, which are slidably mounted in the channels 29, are configured to promote necrosis of prostatic tissue via an electrolytic reaction. As shown in FIG. 16, each of the plurality of electrodes 20 can include a curved tip to ease their deployment out of the electrode assembly 14. Each of the plurality of electrodes 20 can include an uninsulated distal portion 58 configured to act as a site for electrolysis, and may be sufficiently sharp to penetrate the urethral wall. An insulated sheath 60, in the form of a film, membrane, may surround other portions of the electrodes 20. As shown in FIG. 17, the proximal and 30 of the electrode assembly 14 can be operably coupled to an assembly fixture 62, thereby enabling each of the electrodes 20 to be electrically isolated and coupled to its respective outlet.

Figure 18:
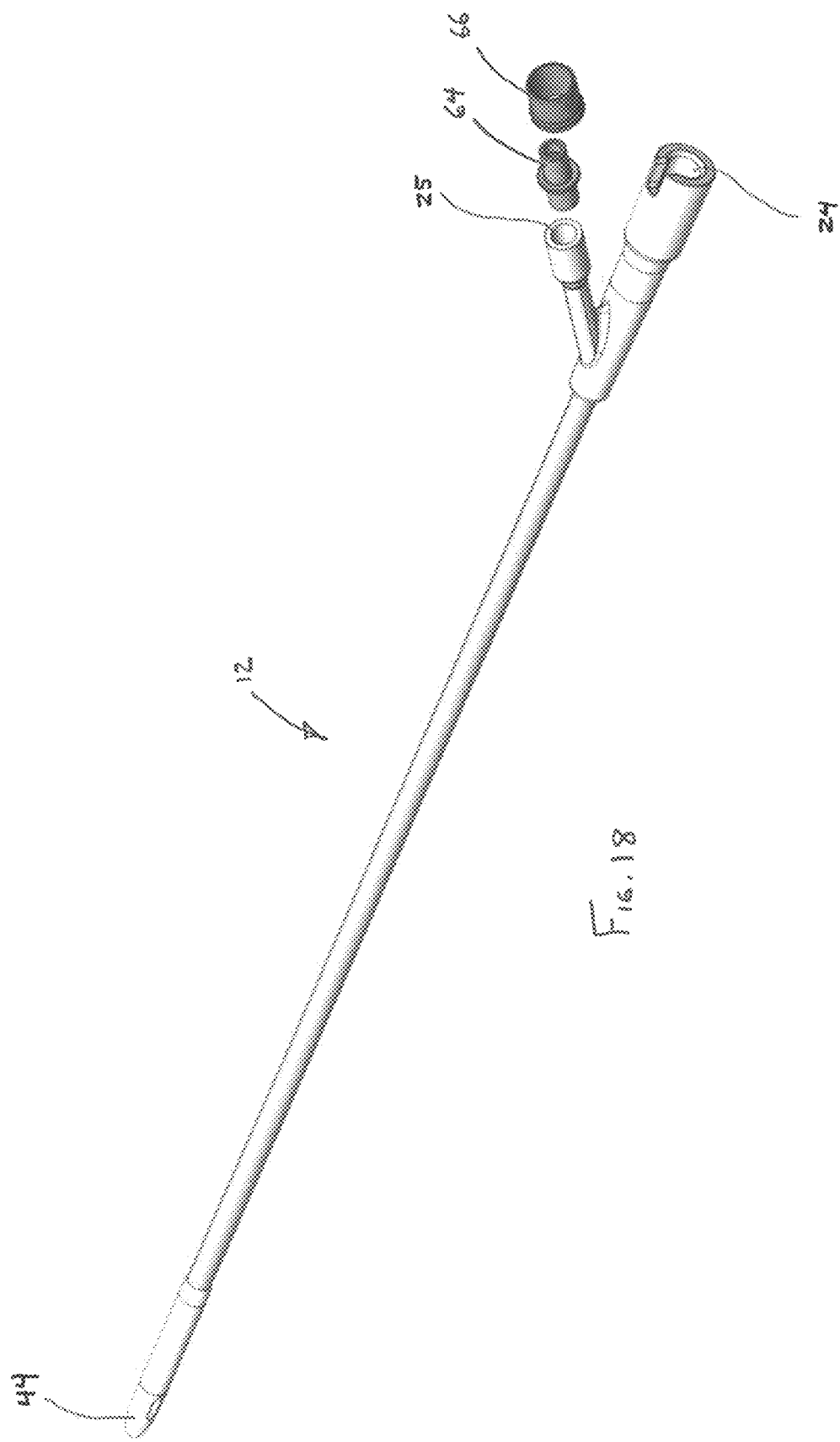
FIG. 18 is an exploded, perspective view depicting a urethral catheter, in accordance with an embodiment of the disclosure.

As shown in FIG. 18, the urethral catheter 12 can define a proximal opening 24 through which the electrode assembly 14 is slidably received. The urethral catheter 12 can further include a catheter inflation port 25, which in some embodiments can include a slip Luer valve 64 and retaining clamp ring 66. The distal end 44 of the urethral catheter 12 can include a blunt, rounded, tapered, or beveled end to ease in insertion of the urethral catheter 12 into a patient. In one embodiment, the urethral catheter 12 can be constructed of silicone, and can be more flexible than the electrode assembly 14. As such, the urethral catheter 12 can serve as a guide for the electrode assembly 14, thereby protecting the urethra 1 from inadvertent trauma during insertion of the less flexible electrode assembly 14.

Figure 19:
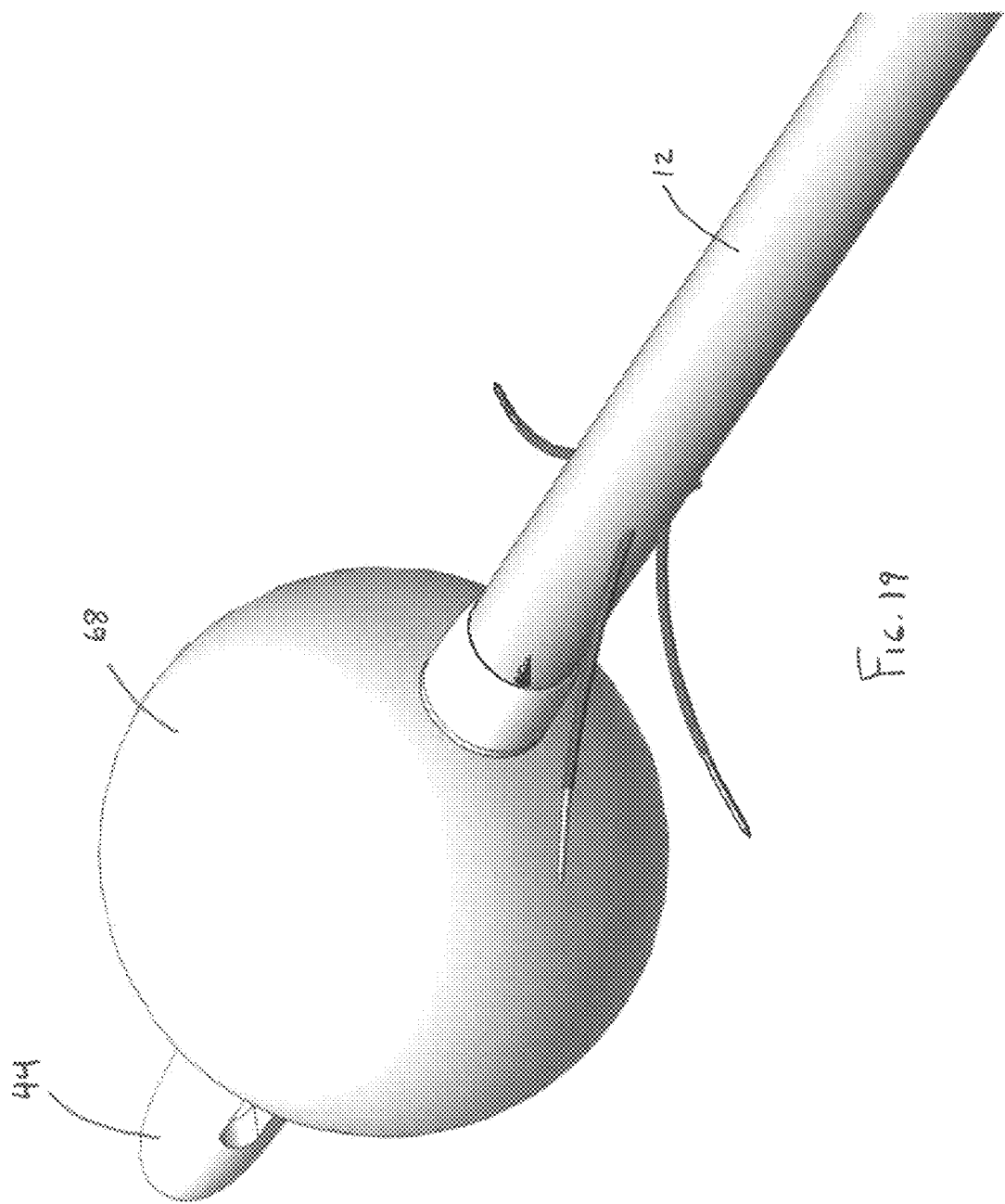
FIG. 19 is a partial, perspective view depicting a urethral catheter having an inflatable balloon, in accordance with an embodiment of the disclosure.
Figure 20:
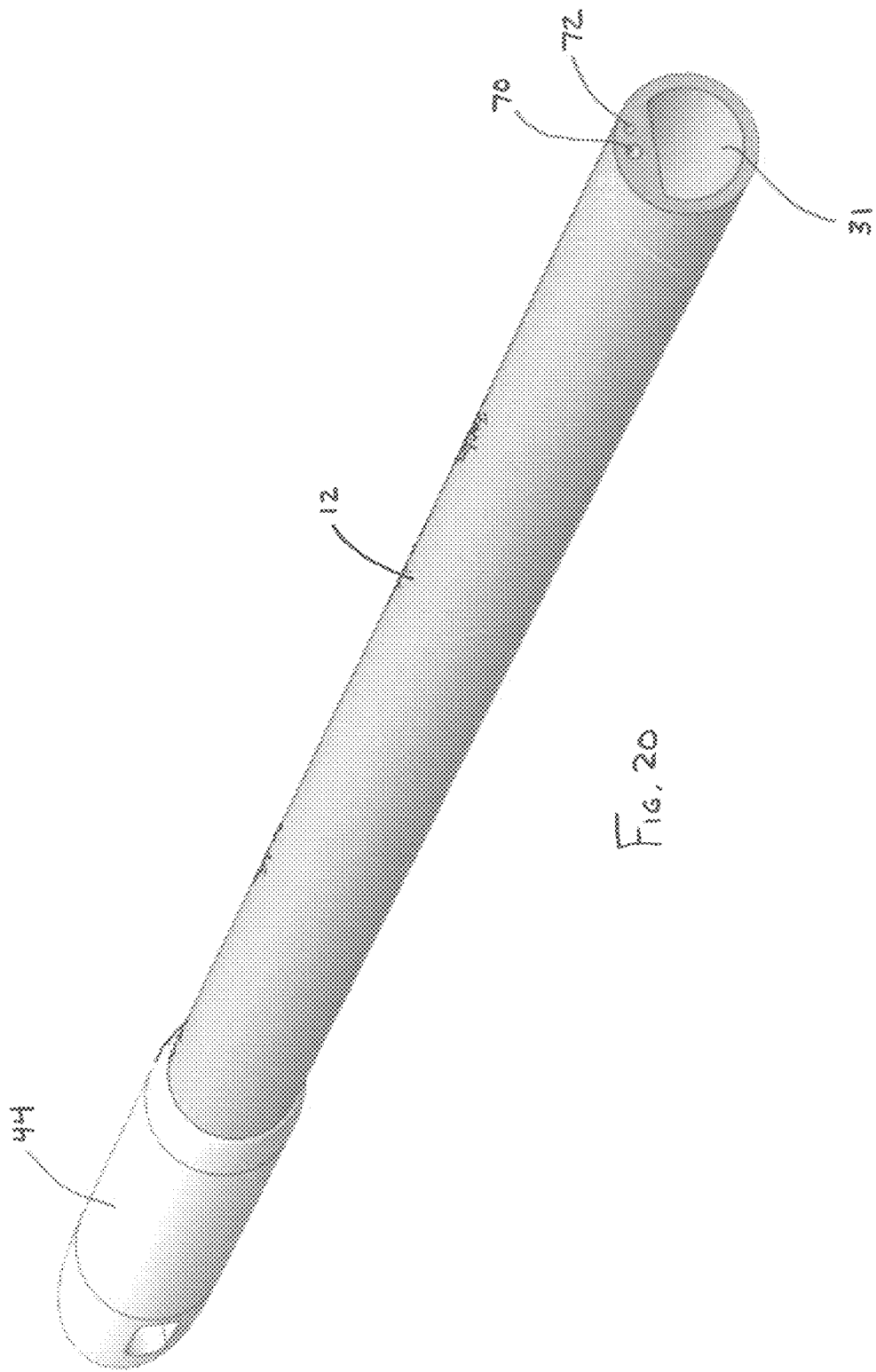
FIG. 20 is a cross sectional, perspective view depicting a urethral catheter including an anti-stretch device, in accordance with an embodiment of the disclosure.

In use, the proximal opening 24 and the catheter inflation port 25 can remain outside of the patient's body. As depicted in FIG. 19, the urethral catheter 12 can include a fixation element in the form of an inflatable balloon 68 adjacent to a distal end 44 thereof, to fix the apparatus 10 in a treatment position. The inflatable balloon 68 is configured to aid in the retention of the urethral catheter 12 within the urethra 1. The inflatable balloon 68 can be inflated with saline, air, or generally any suitable form a fluid. The saline or air can be introduced via the catheter inflation port 25, which is in fluid communication with the inflatable balloon 68 via a fluid conduit 70, as shown in FIG. 20. In one embodiment, the urethral catheter 12 can further include an anti-stretch device 72, such as a wire, configured to inhibit longitudinal expansion and/or contraction, or a change in the overall length, of the urethral catheter 12 during manipulation of the inflatable balloon 68.

Figure 21:
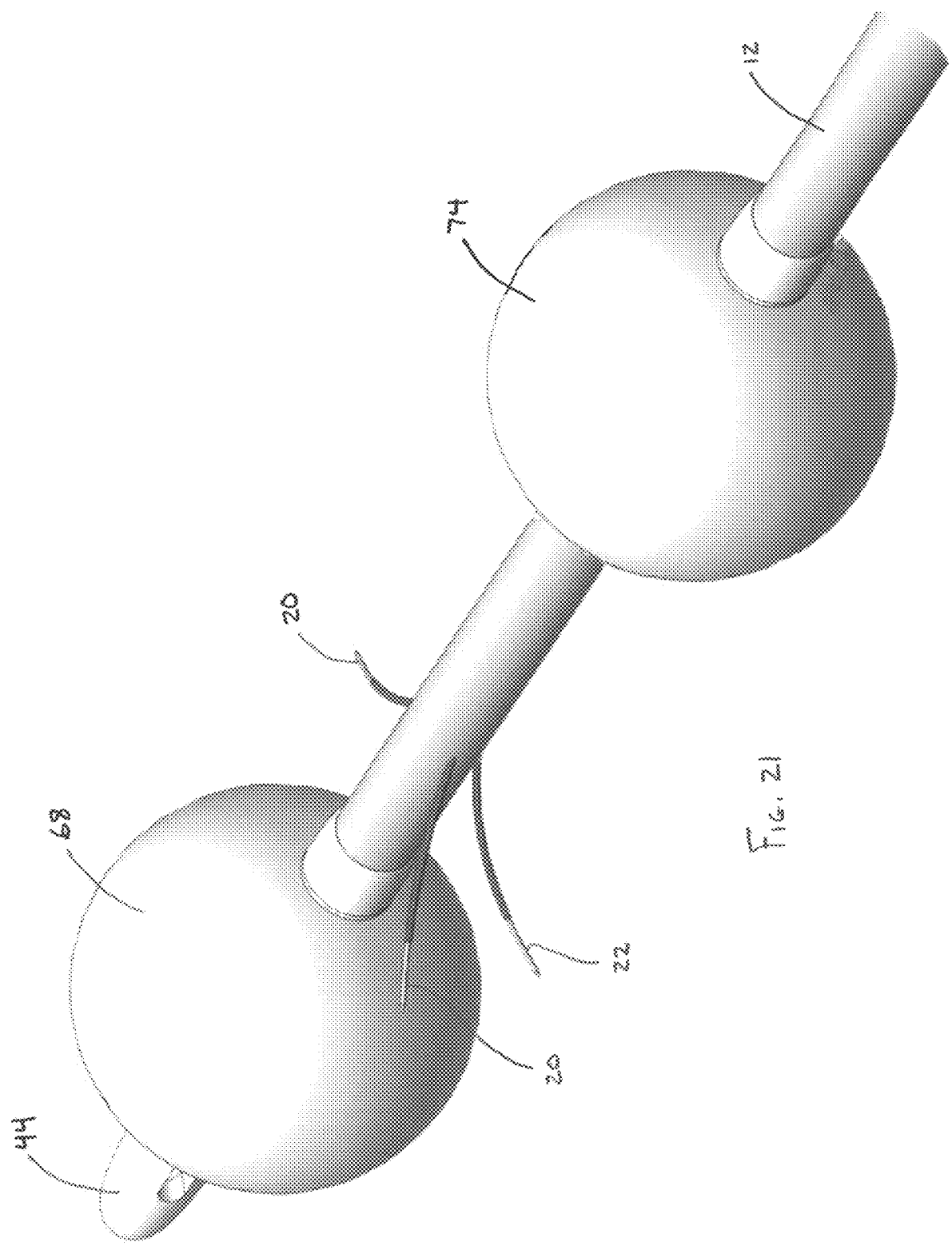
FIG. 21 is a partial, perspective view depicting a urethral catheter having a first inflatable balloon and a second inflatable balloon, in accordance with an embodiment of the disclosure.

As shown in FIG. 21, in some embodiments, the urethral catheter 12 can include a second inflatable balloon 74, such that the first inflatable balloon 68 is positioned distally to an extension of the electrodes 20, 22 along the urethral catheter 12, and the second inflatable balloon 74 is positioned proximally to an extension of the electrodes 20, 22 along the urethral catheter 12. In combination with the anti-stretch device 72, the first inflatable balloon 68 and the second inflatable balloon 74 can serve as an aid in maintaining a desired position of the apparatus 10 during extension of the electrodes 20, 22. In another embodiment, the second inflatable balloon 74 can be disposed such that it is external of the urethra 1 when inflated, thereby serving as a visual indicator of the inflation state of the first inflatable balloon 68.

Figure 22A:
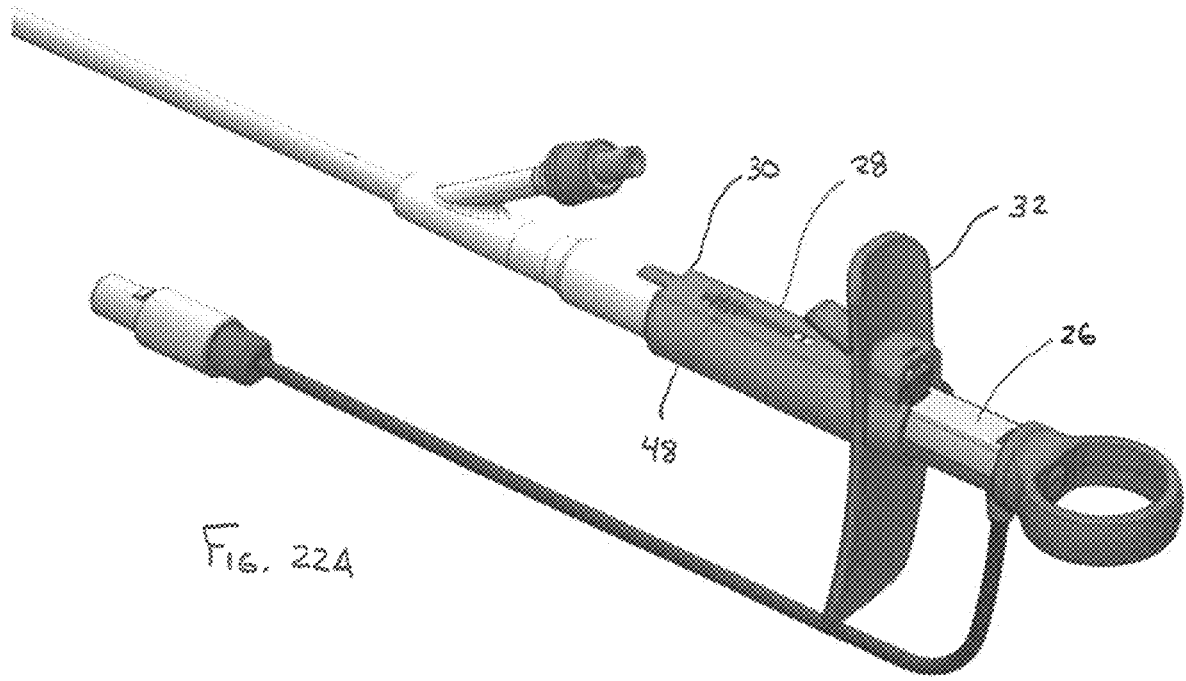
FIGS. 22A-B are perspective views depicting an electrode assembly including a handle, in accordance with an embodiment of the disclosure.
Figure 22B:
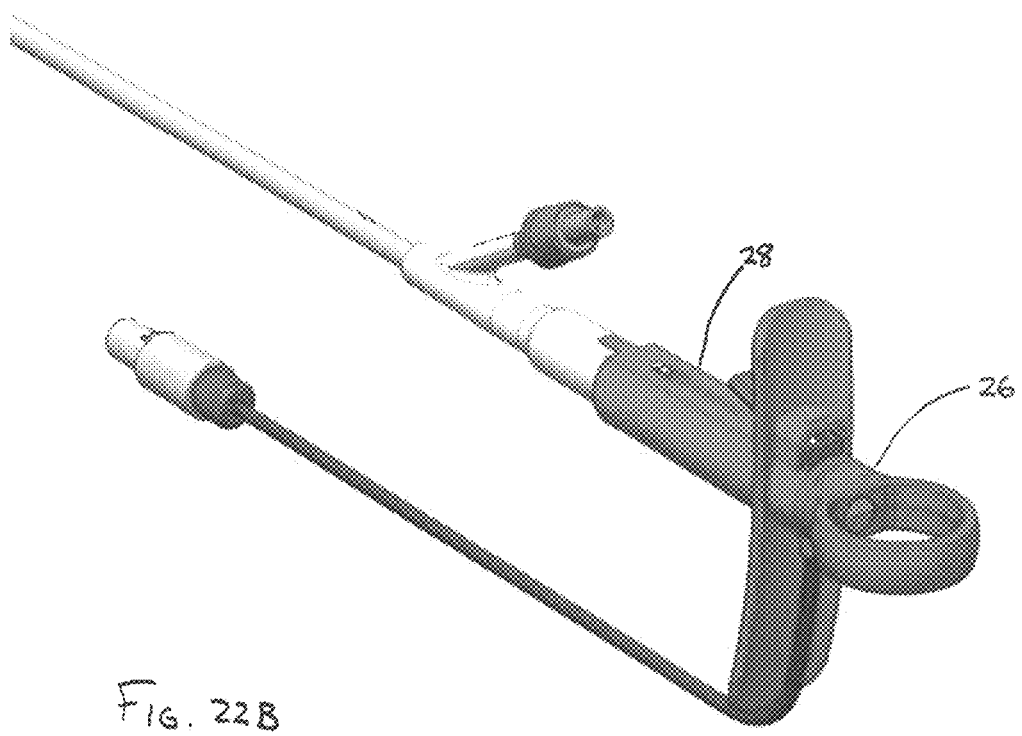

As shown in FIGS. 22A and 22B, the plurality of extendably mounted electrodes 20, 22 are attached at a proximal end thereof to a linear actuatable handle. The linear actuatable handle can be an electrode propeller 26, for example, in the form of a knob or plunger. In some embodiments, the electrode propeller 26 can include a ring, shaped and sized to enable a thumb of the user to be at least partially inserted therein.

The proximal end 30 of the electrode assembly 14 can include a collar 28 configured to interface with the proximal opening 24 of the urethral catheter when the electrode assembly 14 is slidably received within the lumen 31 of the urethral catheter 12. In one embodiment, the collar can define a flange 32 configured be received by a finger of a user, such that linear actuation of the extendable electrodes 20, 22 can be controlled by a user manipulating the electrode propeller 26 relative to the flange 32. FIG. 22A depicts the apparatus in a non-extended position, whereby the electrodes 20, 22 are not extended from the electrode assembly 14. FIG. 22B depicts the apparatus a treatment position, whereby the electrodes are extended from the electrode assembly 14.

As shown in FIG. 23, the collar 28 and the electrode propeller 26 can be joined by a sliding keyed joint 38, thereby inhibiting rotation of the electrode propeller 26 relative to the collar 28. For example, the electrode propeller 26 can include a key 40 configured to be slidingly received within a corresponding keyway 42 defined by the collar 28, thereby inhibiting rotation of the electrode propeller 26 relative to the collar 28. The handle can further include a disengageable stop 36 configured to inhibit actuation of the electrode propeller 26 relative to the collar 28. The handle can further include a fastener 48 configured to fasten the electrode assembly 14 to the urethral catheter 12 when the electrode assembly 14 is slidingly received within the urethral catheter 12. An electrical connector 37 can extend from the handle for connection to a source of electricity 27, thereby supplying power to the electrodes 20, 22.

Now that embodiments have been described, it will be appreciated that some embodiments may have some of the following advantages:

The treatment of a prostatic disease may be minimally invasive.

Treatment times may be less than prior art treatment times, for example no more than 10 minutes, for example no more than 8 minutes or no more than 5 minutes.

The apparatus may be inserted by person with less skill than a urologist, for example a nurse or technician, and may be inserted without the use of transrectal ultrasound guidance.

There may not be a significant increase in the prostate tissue temperature, for example no more than 10 degrees centigrade.

There may not be a significant increase in a length of the urethral catheter, in some embodiments less than a 5% increase in length, and in other embodiments less than a 1% increase in length.

Various embodiments and method of using those embodiments are described in the next paragraphs.

An apparatus for the treatment of a prostatic disease, the apparatus comprising:

a urethral catheter for insertion into a urethra; and an electrode assembly slidingly receivable within the urethral catheter, the electrode assembly comprising a plurality of extendably mounted electrodes for extension into a prostate adjacent the urethra, wherein the plurality of extendably mounted electrodes are for electrolytic generation of at least one of a necrotizing base and a necrotizing acid within the prostate.

An apparatus defined by the preceding paragraph comprising an inflatable balloon adjacent a distal end of the urethral catheter for inflation within a urinary bladder in fluid communication with the urethra, and another inflatable balloon disposed at a proximal end of the urethral bladder and in fluid communication therewith.

An apparatus defined by either one of the preceding paragraphs wherein each of the plurality of extendably mounted electrical electrodes are slidingly mounted and are attached at a proximal end thereof to an electrode propeller that is user actuatable.

An apparatus defined by the preceding paragraph wherein the electrode propeller is linearly actuatable by the user.

An apparatus defined by any one of the preceding paragraphs comprising a collar attached to a proximal end of the electrode assembly and rotationally fixed to the electrode propeller.

An apparatus defined by the preceding paragraph wherein the collar and the electrode propeller are joined at a sliding keyed joint.

An apparatus defined by any one of the preceding paragraphs wherein a distal end of the urethral catheter comprises a plurality of electrode passageways connecting an interior and exterior of thereof, and the urethral catheter and the electrode assembly are configured to engage with a predetermined rotational orientation to each other for alignment of the plurality of extendably mounted electrodes with the plurality of electrode passageways.

An apparatus defined by the preceding paragraph wherein the urethral catheter and the electrode assembly can be joined to form a sliding keyed joint.

An apparatus defined by any one of the preceding paragraphs comprising a flange attached to the collar, wherein the flange and the electrode propeller are cooperatively arranged for the flange to be received by a finger of a hand and the electrode propeller to be actuated by the thumb of the hand when the flange is so received.

An apparatus defined by any one of the preceding paragraphs comprising a disengageable stop arrange to prevent actuation of the electrode propeller until disengaged.

An apparatus defined by any one of the preceding paragraphs wherein at least one of the electrode assembly and the urethral catheter comprise a fastener configured to fasten the electrode assembly to the urethral catheter when the electrode assembly is slidingly received within the urethral catheter.

An apparatus defined by any one of the preceding paragraphs comprising a source of the electricity and a controller for the source of the electricity.

An apparatus defined by the preceding paragraph comprising a monitor configured to generate electrical parameter information indicative of an electrical parameter associated with electricity supplied to the plurality of expendably mounted electrodes, wherein the controller is configured to control the electricity supplied to the plurality of expendably mounted electrodes depending on the electrical parameter information.

An apparatus defined by any one of the preceding paragraphs wherein the controller is configured to change the electricity during the electrolytic generation of at least one of the necrotizing base and the necrotizing acid within the prostate.

An apparatus defined by any one of the the preceding paragraphs wherein the controller has a plurality of electrical modes for a plurality of prostates quality types.

An apparatus defined by any one of the preceding paragraphs wherein the electricity is a direct current.

An apparatus defined by any one of the proceeding paragraphs wherein the plurality of extendably mounted electrodes comprises an electrode within an insulating sheath defining at least two uninsulated distal portions of the electrode.

An apparatus defined by any one of the preceding paragraphs wherein each of the plurality of extendably mounted electrodes comprise a rounded tip.

An apparatus defined by any one of the preceding paragraphs wherein each of the plurality of extendably mounted electrodes has a cruciform transverse section.

An apparatus defined by any one of the preceding paragraphs comprising a chemical introducible by at least one of the plurality of electrodes into the prostate.

An apparatus defined by any one of the preceding paragraphs defining a plurality of channels for each electrode for selective disposition of each electrode within the prostate.

An apparatus defined by any one of the preceding paragraphs wherein at least one of the plurality of extendably mounted electrodes is more extendable than at least another one of the plurality of extendable lengths.

An apparatus defined by any one of the preceding paragraphs wherein the urethral catheter is more flexible than the electrical assembly.

An apparatus defined by any one of the proceeding paragraphs wherein the urethral catheter comprises a fixation element.

An apparatus defined by any one of the preceding paragraphs wherein the urethral catheter comprises a Foley catheter.

A method for treatment of a prostatic disease using an apparatus as defined by any of the preceding paragraphs, the method comprising:

inserting an urethral catheter into a urethra;

inserting an electrode assembly into the urethra, the electrode assembly comprising a plurality of extendably mounted electrodes;

extending the plurality of extendably mounted electrodes into a prostate adjacent the urethra;

supplying electricity to the plurality of extendably mounted electrodes wherein at least one of a necrotizing base and a necrotizing acid is generated within the prostate.

A method defined by the preceding paragraph wherein the electrode assembly is disposed within the urethral catheter during insertion of the urethral catheter into the urethra.

A method defined by the preceding paragraph wherein the electrode assembly is inserted into the urethral catheter so inserted into the urethra.

A method defined by any one of the preceding paragraphs wherein the urethral catheter is more flexible than the electrode assembly.

A method defined by any one of the preceding paragraphs wherein extending the plurality of electrodes into the prostate adjacent the urethra comprising a user actuating an electrode propeller attached to the plurality of electrodes to extend a plurality of tips of the plurality of electrodes out of the electrode assembly and into the prostate.

A method defined by the preceding paragraph comprising the step of rotationally fixing a collar attached to a proximal end of the electrode assembly to the electrode propeller.

A method defined by the preceding paragraph comprising the step of joining the electrode propeller and the collar to form a sliding keyed joint.

A method defined by any one of the preceding paragraphs comprising disengaging a stop arranged to prevent actuation of the electrode propeller to enable actuation of the electrode propeller.

A method defined by any one of the preceding paragraphs comprising the step of generating electrical parameter information indicative of electricity supplied to the plurality of extendably mounted electrodes, wherein the controller is configured to control the electricity supplied to the plurality of extendably mounted electrodes depending on the electrical parameter information.

A method defined by the preceding paragraph comprising the step of changing the electricity supplied to the plurality of extendably mounted electrodes during the electrolytic generation of at least one of the necrotizing base and the necrotizing acid.

A method defined by any one of the preceding paragraphs comprising the step of selecting one of a plurality of electricity supply modes, the plurality of electricity supply modes being for treatment of a plurality of prostate quality types.

A method defined by any one of the preceding paragraphs comprising the step of changing the disposition of at least one of the plurality of extendably mounted electrodes within the prostate and supplying electricity to the at least one of the plurality of extendably mounted electrodes.

A method defined by any one of the preceding paragraphs comprising the step of introducing a chemical to a volume of the prostate, wherein the chemical belongs to a group of chemicals comprising a chemical that counters at least one of the necrotizing acid and the necrotizing base, and a necrotizing chemical that reduces or increases the pH within the prostate.

A method defined by the preceding paragraph comprising introducing the chemical into the prostate via a lumen in at least one of the plurality of electrodes.

A method defined by any one of the preceding paragraphs comprising using electromyography to detect an sphincter urethrae membranaceae adjacent the urethra and position the plurality of electrodes relative to the sphincter urethrae membranaceae.

A method defined by any one of the preceding paragraphs comprising inflating a first balloon attached to a distal end of the urethral catheter within a urinary bladder in fluid communication with the urethra, and a second balloon disposed adjacent a proximal end of the urethral catheter and in fluid communication with the first balloon.

A method defined by any one of the preceding paragraph comprising introducing a fluid into a balloon attached to a distal end of the urethral catheter and disposed within a urinary bladder in fluid communication with the urethra, and monitoring the pressure of the fluid introduced into the balloon.

A method defined by any one of the preceding paragraphs comprising the step of reading an attached identification tag.

A method defined by any one of the preceding paragraphs wherein the step of supplying the electricity to the plurality of extendably mounted electrodes comprises supplying electricity to the plurality of electrodes asynchronously.

A method defined by any one of the preceding paragraphs comprising the step of withdrawing the plurality of extendable electrodes from the prostate and extending another plurality of extendably mounted electrodes of another electrode assembly into the prostate at a different prostate position.

A method defined by any one of the preceding paragraphs comprising the step of activating a fixation element of the urethral catheter.

A method defined by any one of the preceding paragraphs wherein the urethral catheter comprises a Foley catheter.

An apparatus for the treatment of a prostatic disease, the apparatus comprising an electrode assembly slidingly receivable within a urethral catheter, the electrode assembly comprising a plurality of extendably mounted electrodes for extension through urethral tissue and into a prostate, wherein the plurality of extendably mounted electrodes are for electrolytic generation of at least one of a necrotizing base and a necrotizing acid within the prostate.

An apparatus or method defined by the preceding paragraph wherein the plurality of extendably mounted electrodes comprises at least one electrolytically corrodible.

A urethral catheter comprising a distally attached inflatable balloon for inflation within a body and a proximally attached inflatable balloon in fluid communication with the distally attached inflatable balloon for disposition exterior of the body when the distally attached inflatable balloon is so inflated within the body.

Variations and/or modifications may be made to the embodiments described without departing from the spirit or ambit of the invention. While the illustrated embodiments comprise a urethral catheter, alternative embodiments may not comprise the urethral catheter, which may be a separately supplied for the procedure, for example. While the urethral catheter in the present embodiments is a Foley catheter or a variation thereof, generally any suitable urethral catheter may be used, examples of which include but are not limited to an intermittent catheter, and a coudé catheter. The present embodiments are, therefore, to be considered in all respects as illustrative and not restrictive. Reference to a feature disclosed herein does not mean that all embodiments must include the feature.

In the claims which follow and in the preceding description of the invention, except where the context requires otherwise due to express language or necessary implication, the word "comprise" or variations such as "comprises" or "comprising" is used in an inclusive sense, that is to specify the presence of the stated features but not to preclude the presence or addition of further features in various embodiments of the invention.

The invention claimed is:

1. A prostatic treatment apparatus for treating a prostate in a body of a patient, the prostate generally surrounding a urethra which is connected to a bladder of the patient, the apparatus comprising:
a urethral catheter including:
a proximal portion having a first port and a second port each configured to be positioned external to the body of the patient;
a distal portion having an inflatable balloon configured to be advanced via the urethra into the bladder and in fluid communication with the first port; and
a lumen extending from the second port to proximate the distal portion, the lumen having a cross-sectional shape;
an electrode assembly including:
a shaft configured to be slidably received within lumen of the urethral catheter, the shaft having a cross-sectional shape that interlocks with the cross-sectional shape of the lumen to inhibit rotation of the shaft within the lumen, and a plurality of channels defined within the shaft, each channel having a corresponding extendable electrode disposed therein;
a proximal portion having a collar at a proximal end of the shaft that is configured to interface with the second port when the electrode assembly is slidably received within the lumen, a flange structure protruding from the collar, and an electrode actuator proximal of the flange structure, the electrode actuator operably connected to a proximal portion of the extendable electrodes and configured to control linear actuation of the extendable electrodes, wherein the collar and the electrode actuator are interfaced via a keyed structure to inhibit rotation of the electrode actuator relative to the collar; and an electrode tip at a distal end of the shaft and having a plurality of ports defined therein, each port interfacing with a corresponding channel in the lumen and configured to project a distal end of the corresponding extendable electrode outward through the urethral catheter and into the prostate in response to linear actuation of the electrode actuator, the corresponding extendable electrode being extended in a predefined rotational orientation relative to the keyed structure and proximal to the inflatable balloon; and a power source electrically coupled to the extendable electrodes and configured to deliver direct current to the prostate when the extendable electrodes are extended into the prostate to promote necrosis of the prostate via an electrolytic reaction.

2. The prostatic treatment apparatus of claim 1, wherein the electrode actuator includes a ring structure configured to enable a thumb of a user to be at least partially inserted therein, wherein the flange structure is configured to interface with one or more fingers of the user, and wherein the linear actuation of the extendable electrodes is controlled by the user manipulating the ring relative to the flange.

3. The prostatic treatment apparatus of claim 1, further comprising a disengageable stop configured to inhibit actuation of the electrode actuator relative to the collar.

4. The prostatic treatment apparatus of claim 1, further comprising a fastener configured to secure the electrode assembly relative to the urethral catheter when the electrode assembly is slidingly received within the urethral catheter.

5. The prostatic treatment apparatus of claim 1, further comprising a second inflatable balloon configured to be positioned outside the urethra and in fluid communication with the first port.

6. The prostatic treatment apparatus of claim 1, the power source comprises:
a source of the direct current;
a controller for the source of the direct current; and
a monitor configured to generate electrical parameter information indicative of an electrical parameter associated with electricity supplied to the plurality of extendable electrodes,
wherein the controller is configured to control the direct current supplied to the plurality of extendable electrodes depending on the electrical parameter information.

7. The prostatic treatment apparatus of claim 6, wherein the controller is configured to change the delivery of direct current during electrolytic generation of at least one of a necrotizing base and a necrotizing acid within the prostate.

8. The prostatic treatment apparatus of claim 1, wherein each of the plurality of extendable electrodes comprises an electrode within an insulating sheath defining at least two uninsulated distal portions of the electrode that are configured to be extended out of the electrode tip.

9. The prostatic treatment apparatus of claim 1, further comprising a channel in one of the urethral catheter, and the electrode assembly is configured to introduce a chemical into the prostate proximate at least one of the plurality of extendable electrodes.

10. The prostatic treatment apparatus of claim 1, wherein at least one of the plurality of extendable electrodes is configured to be extended further into the prostate than at least another one of the plurality of extendable electrodes.

11. The prostatic treatment apparatus of claim 1, wherein the cross-sectional shape of the lumen of the urethral catheter and the cross-sectional shape of the shaft of the electrode assembly are corresponding D-shapes.

12. The prostatic treatment apparatus of claim 1, wherein the electrode tip is replaceable, and the apparatus includes a plurality of different replaceable electrode tips, each electrode tip having the plurality of ports positioned to provide a different predefined rotational orientation of the ports relative to the keyed structure.

13. The prostatic treatment apparatus of claim 1, wherein the shaft of the electrode assembly further comprises an anti-torsion strip extending along the shaft, the anti-torsion strip having a generally rectangular cross-sectional shape with an aspect ratio of greater than 4 to 1 and made of a material stiffer than a material of the shaft to increase torsion resistance of the shaft.

14. The prostatic treatment apparatus of claim 13, wherein the anti-torsion strip is made of a metal material and is configured to be selectively pre-formed into a curved longitudinal shape prior to insertion of the electrode assembly into the urethral catheter.

15. The prostatic treatment apparatus of claim 1, wherein the urethral catheter further includes a second lumen extending from the distal portion to the proximal portion and having an anti-stretch device disposed therein made of a material that is stiffer than a material of the urethral catheter to decrease a longitudinal stretch of the urethral catheter in response to the linear actuation of the electrode actuator.

16. The prostatic treatment apparatus of claim 15, wherein the anti-stretch device is made of a metal material and is configured to be selectively pre-formed into a curved longitudinal shape prior to insertion of the urethral catheter into the urethra.

17. The prostatic treatment apparatus of claim 1, wherein the shaft of the electrode assembly further comprises a sleeve assembly that is over-jacketed about the shaft to retain the plurality of extendable electrodes within corresponding ones of the plurality of channels.

18. A prostatic treatment apparatus for treating a prostate in a body of a patient, the prostate generally surrounding a urethra which is connected to a bladder of the patient, the apparatus comprising:
a urethral catheter including:
a proximal portion having a first port and a second port each configured to be positioned external to the body of the patient;
a distal portion having an inflatable balloon configured to be advanced via the urethra into the bladder and in fluid communication with the first port; and
a lumen extending from the second port to proximate the distal portion, the lumen having a cross-sectional shape;
an electrode assembly including:
a shaft configured to be slidably received within lumen of the urethral catheter, the shaft having:
a cross-sectional shape that interlocks with the cross-sectional shape of the lumen to inhibit rotation of the shaft within the lumen,
a plurality of channels defined within the shaft, each channel having a corresponding extendable electrode disposed therein,
an anti-torsion strip extending along the shaft, the anti-torsion strip having a generally rectangular cross-sectional shape and made of a metal material stiffer than a material of the shaft to increase torsion resistance of the shaft, and
a sleeve assembly that is over-jacketed about the shaft to retain the extendable electrodes and the anti-torsion strip within the shaft;

a proximal portion having a collar at a proximal end of the shaft that is configured to interface with the second port when the electrode assembly is slidably received within the lumen, and an electrode actuator operably connected to a proximal portion of the extendable electrodes and configured to control linear actuation of the extendable electrodes; and an electrode tip at a distal end of the shaft and having a plurality of ports defined therein, each port interfacing with a corresponding channel in the lumen and configured to project a distal end of the corresponding extendable electrode outward through the urethral catheter proximal to the inflatable balloon and into the prostate in response to linear actuation of the electrode actuator; and a power source electrically coupled to the extendable electrodes and configured to deliver direct current to the prostate when the extendable electrodes are extended into the prostate to promote necrosis of the prostate via an electrolytic reaction.

19. The prostatic treatment apparatus of claim 18, wherein the urethral catheter further includes a second lumen extending from the distal portion to the proximal portion and having an anti-stretch device disposed therein made of a material that is stiffer than a material of the urethral catheter to decrease a longitudinal stretch of the urethral catheter in response to the linear actuation of the electrode actuator.

20. The prostatic treatment apparatus of claim 19, wherein the anti-stretch device is made of a metal material and at least one of the anti-torsion strip and the anti-stretch device is configured to be selectively pre-formed into a curved longitudinal shape prior to insertion into the urethra.

21. The prostatic treatment apparatus of claim 18, wherein the collar and the electrode actuator are interfaced via a keyed structure to inhibit rotation of the electrode actuator relative to the collar, and wherein each corresponding extendable electrode being extended in a predefined rotational orientation relative to the keyed structure.

* * * * *